US008183862B2

(12) United States Patent
Endo et al.

(10) Patent No.: US 8,183,862 B2
(45) Date of Patent: May 22, 2012

(54) EDDY CURRENT TESTING DEVICE

(75) Inventors: Hisashi Endo, Hitachi (JP); Akira Nishimizu, Tokai (JP); Hirofumi Ouchi, Mito (JP); Yoshio Nonaka, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 448 days.

(21) Appl. No.: 12/389,499

(22) Filed: Feb. 20, 2009

(65) Prior Publication Data

US 2009/0230952 A1 Sep. 17, 2009

(30) Foreign Application Priority Data

Mar. 11, 2008 (JP) .................................. 2008-060868

(51) Int. Cl.
*G01N 27/82* (2006.01)
(52) U.S. Cl. ......... 324/238; 324/233; 324/236; 324/232
(58) Field of Classification Search ....................... 324/207.11–207.26, 228–243
See application file for complete search history.

(56) References Cited

U.S. PATENT DOCUMENTS

| 5,006,800 A * | 4/1991 | Hedengren et al. ............ 324/233 |
| 5,059,905 A * | 10/1991 | Drits ............................ 324/233 |
| 2007/0120560 A1 * | 5/2007 | Rempt ........................... 324/238 |
| 2008/0159619 A1 * | 7/2008 | Suh et al. ...................... 382/152 |
| 2009/0009162 A1 | 1/2009 | Nishimizu et al. |

FOREIGN PATENT DOCUMENTS

| JP | 63-81262 A | 4/1988 |
| JP | 3-167470 A | 7/1991 |
| JP | 8-220073 A | 8/1996 |
| JP | 9-189682 A | 7/1997 |
| JP | 10-282064 A | 10/1998 |
| JP | 2005-201778 A | 7/2005 |
| JP | 2006-145296 A | 6/2006 |
| JP | 2006-194661 A | 7/2006 |
| JP | 2007-147525 A | 6/2007 |
| JP | 2007-171199 A | 7/2007 |
| JP | 2007-183231 A | 7/2007 |

OTHER PUBLICATIONS

Nishimizu et al., Development of Flexible Multi Eddy Current Testing Sensor, The 8th Symposium on Nondestructive Surface Testing (2005), pp. 139-142.

\* cited by examiner

*Primary Examiner* — Arleen M Vazquez
(74) *Attorney, Agent, or Firm* — Mattingly & Malur, PC

(57) ABSTRACT

An eddy current testing device which confirms that a change in characteristics of a target object is detected regardless of the magnitude of the change and specifying the position of a portion from which the change is detected. The device uses an eddy current probe to inspect a bent portion of a metal body, and has an inspection controller and a display unit. The inspection controller calculates a phase angle of a signal detected by the eddy current probe and generates flaw identification image data that indicates an area (or an area of the signal detected and determined to correspond to a flaw signal, based on the phase angle of the detected signal) of a flaw signal in coordinates in which the position of the portion of the target object is plotted along a coordinate axis. The display unit displays the flaw identification image data.

9 Claims, 16 Drawing Sheets

SCANNING DIRECTION

☐ AREA IN WHICH NO FLAW SIGNAL PRESENTS
■ AREA IN WHICH FLAW SIGNAL PRESENTS

PHASE ANGLE $\theta 1$ OF SIGNAL DETECTED BY FIRST DETECTION COIL

☐ AREA IN WHICH NO FLAW SIGNAL PRESENTS
■ AREA IN WHICH FLAW SIGNAL PRESENTS

EDDY CURRENT TESTING DEVICE

BACKGROUND OF THE INVENTION

1. Field of the Invention

The present invention relates to an eddy current testing device for evaluating a change in characteristics of a target object to be inspected, such as a crack and a change in a property of a material of the target object, and more particularly to an eddy current testing device that uses an eddy current probe having a mutual induction type standard comparison scheme to evaluate a change in characteristics of a target object to be inspected.

2. Description of the Related Art

A method for inspecting a metal body (which is a target object) using an eddy current is to supply an alternating current (exciting current) to a coil provided in an eddy current probe, cause the coil to generate an alternating magnetic flux, cause the eddy current probe to approach the metal body and generate an eddy current, and detect a signal indicating turbulence of the eddy current. The eddy current varies depending on conductivity, permeability and the like of the target object. It is therefore possible to evaluate a change in characteristics of the target object (such as a crack of the target object, a change in a property of a material of the target object, and the like) to be inspected under the condition that the eddy current probe is not in contact with the target object. Specifically, the eddy current probe is used to detect a standard detection signal from a well-conditioned standard sample piece in advance, and a difference between a signal detected from the target object and the standard detection signal is displayed on a screen. An inspector can confirm a change in the characteristics of the target object by viewing the display screen.

A Lissajous pattern showing amplitude and a phase angle of the detected signal is known as a method for displaying the detected signal. Specifically, the detected signal (voltage) is converted into an X component voltage Vx and a Y component voltage Vy. The X component voltage Vx has the same phase as that of the standard signal. The Y component voltage Vy is represented in a direction perpendicular to a direction in which the X component voltage Vx is represented. After the conversion, the X component voltage Vx is plotted along an X axis, and the Y component voltage Vy is plotted along a Y axis, to represent the amplitude |V| and phase angle θ of the detected signal (refer to the following expressions (1) and (2)). The inspector can determine whether or not a flaw signal is detected based on the shape of a Lissajous pattern.

$$|V|=(Vx^2+Vy^2)^{-1/2} \quad (1)$$

$$\theta=\tan^{-1}(Vy/Vx) \quad (2)$$

In recent years, a scanning mechanism for moving an eddy current probe along a target object has been used, or a multi-coil probe having coils regularly arranged has been used as an eddy current probe, to inspect a wide area of the target object. In those cases, since the position of a portion of the target object, from which a flaw signal is detected, cannot be confirmed based on a Lissajous pattern, a display method (C scope) is used to indicate the amplitude of the detected signal by means of grayscale shading in two dimensional coordinates in which the position of the portion of the target object is plotted along a coordinate axis (refer to, for example, Non-Patent Document 1 (Nishimizu, etc., "Development of Flexible Multi Eddy Current Testing Sensor", The 8th Symposium on Nondestructive Surface Testing (2005), pp. 139-142).

SUMMARY OF THE INVENTION

It is, however, possible to improve the aforementioned conventional technique. That is, the C scope displays the amplitude of the detected signal by means of grayscale shading in the two dimensional coordinates in which the position of a portion of the target object (from which the signal is detected) is plotted along the coordinate axis. The amplitude of the detected signal is proportional to the magnitude (for example, the depth of a crack or the like) of a change in the characteristics of the target object. For example, when the change in the characteristics of the target object is large, an indicator signal remarkably appears. This makes it possible to confirm that the change in the characteristics is detected, and to specify the position of the portion from which the change in the characteristics is detected. On the other hand, when the change in the characteristics of the target object is small, the indicator signal is hidden due to a signal (for example, a lift-off signal or the like) caused by the state of the surface of the target object or by the shape of the target object. In this case, it is difficult to accurately determine whether or not the change in the characteristics is detected.

An object of the present invention is to provide an eddy current testing device capable of confirming that a change in characteristics of a target object is detected regardless of the magnitude of the change, and specifying the position of a portion from which the change in the characteristics of the target object is detected.

(1) In order to accomplish the object, an eddy current testing device according to the present invention comprises: an eddy current probe for inspecting a change in characteristics of a target object; phase angle calculation means for calculating a phase angle of a signal detected by the eddy current probe; image data generator for generating image data that indicates the phase angle in coordinates in which at least one of the position of a portion from which the signal is detected, and a time when the signal is detected from the portion, is plotted along a coordinate axis, or generating image data that indicates information based on the phase angle in the coordinates; and output means for outputting the image data generated by the image data generator.

The eddy current testing device according to the present invention generates the image data that indicates the phase angle (or information based on the phase angle) of the detected signal in the coordinates in which, for example, the position of the portion from the signal is detected (or time when the signal is detected from the portion) is plotted along the coordinate axis. The eddy current testing device according to the present invention causes the output means (for example, a monitor, printer, or the like) to output and display the image data. Therefore, an inspector can determine, based on the phase angle of the detected signal displayed with the position of the portion, whether or not the change (for example, a crack) in the characteristics of the target object is detected. The phase angle of the detected signal depends on the shape of the crack, the direction in which the crack extends, and the like, regardless of the depth of the crack. It is therefore possible to confirm that the change in the characteristics of the target object is detected regardless of the magnitude of the change in the characteristics of the target object and to specify the position of the portion from which the change in the characteristics of the target object is detected.

(2) The eddy current testing device described in item (1) preferably further comprises noise removal means for removing a noise signal having a frequency within a preset predetermined frequency band or a noise signal having amplitude lower than preset predetermined amplitude from the signal detected by the eddy current probe, wherein the phase angle calculation means calculates a phase angle of the detected signal after the noise signal is removed from the detected signal by the noise removal means.

(3) The eddy current testing device described in item (1) preferably further comprises means for differentiating between a signal detected from a certain portion of the target object and a signal detected from a portion close to the certain portion or between a signal detected at a certain time and a signal detected at a time close to the certain time, wherein the phase angle calculation means calculates a phase angle of the differentiated detected signals.

(4) In the eddy current testing device described in any of items (1), the image data generator preferably generates image data that indicates the phase angle of the detected signal, which is calculated by the phase angle calculation means, by means of chromaticity or brightness of pixels.

(5) In the eddy current testing device described in item (1), the eddy current probe has at least one excitation coil, a first detection coil and a second detection coil, the first detection coil being arranged with the excitation coil in a direction, the second detection coil being arranged with the excitation coil in another direction; the phase angle calculation means calculates a first phase angle of a first signal detected by the first detection coil and a second phase angle of a second signal detected by the second detection coil; the image data generator generates first image data and second image data, the first image data indicating the first phase angle in coordinates in which at least one of the position of a portion of the target object from which the first signal is detected, and a time when the first signal is detected from the portion, is plotted along a coordinate axis, the second image data indicating the second phase angle in coordinates in which at least one of the position of a portion of the target object from which the second signal is detected, and a time when the second signal is detected from the portion, is plotted along a coordinate axis; and the output means outputs the first image data and the second image data generated by the image data generator.

The eddy current testing device according to the present invention generates the first image data that indicates the first phase angle of the first signal detected by the first detection coil in the coordinates in which, for example, the position of the portion of the target object from which the first signal is detected (or the time when the first signal is detected from the portion) is plotted along the coordinate axis. Also, the eddy current testing device according to the present invention generates the second image data that indicates the second phase angle of the second signal detected by the second detection coil in the coordinates in which, for example, the position of the portion of the target object from which the second signal is detected (or the time when the second signal is detected from the portion) is plotted along the coordinate axis. The eddy current testing device causes the output means (for example, a monitor, printer, or the like) to output and display the image data. Therefore, an inspector can determines, based on the relationship between the first phase angle of the first signal detected by the first detection coil and displayed with the position of the portion of the target object, and the second phase angle of the second signal detected by the second detection coil and displayed with the position of the portion of the target object, whether or not the change (for example, a crack) in the characteristics of the target object is detected. It is therefore possible to confirm that the change in the characteristics of the target object is detected regardless of the magnitude of the change in the characteristics of the target object and to specify the position of the portion from which the change in the characteristics of the target object is detected.

(6) In the eddy current testing device described in item (1), the eddy current probe has at least one excitation coil, a first detection coil and a second detection coil, the first detection coil being arranged with the excitation coil in a direction, the second detection coil being arranged with the excitation coil in another direction; the phase angle calculation means calculates a first phase angle of a first signal detected by the first detection coil and a second phase angle of a second signal detected by the second detection coil; the image data generator determines whether or not the first detected signal and the second detected signal correspond to a change in the characteristics of the target object based on the relationship between the first phase angle and the second phase angle, and generates image data that indicates an area of the signal determined to correspond to the change in the characteristics of the target object by the determination means in coordinates in which at least one of the position of a portion of the target object from which the signal is detected, and a time when the signal is detected from the portion, is plotted along a coordinate axis; and the output means outputs the image data generated by the image data generator.

The eddy current testing device according to the present invention determines whether or not the detected signals correspond to the change (for example, a crack) in the characteristics of the target object based on the relationship between the first phase angle of the first signal detected by the first detection coil and the second phase angle of the second signal detected by the second detection coil. The eddy current testing device according to the present invention then generates the image data that indicates the area of the detection signal determined to correspond to the change in the characteristics of the target object in the coordinates in which, for example, the position of the portion from which the signal is detected (or the time when the signal is detected from the portion) is plotted along the coordinate axis. The eddy current testing device causes the output means (for example, a monitor, printer or the like) to output and display the image data. It is therefore possible to confirm that the change in the characteristics of the target object is readily detected regardless of the magnitude of the change in the characteristics of the target object and to specify the position of the portion from which the change in the characteristics of the target object is detected.

(7) The eddy current testing device described in item (6) preferably further comprises storage means for storing data that indicates a preset predetermined standard area in coordinates in which the first phase angle of the first signal detected by the first detection coil and the second phase angle of the second signal detected by the second detection coil are plotted along coordinate axes, wherein the image data generator determines whether or not the first and second detected signals correspond to the change in the characteristics of the target object by determining whether or not the first phase angle and the second phase angle are included in the predetermined standard area.

(8) In the eddy current testing device described in item (5), the eddy current probe has a flexible substrate mounting the excitation coil, the first detection coil and the second detection coil thereon.

(9) In the eddy current testing device described in item (6), the eddy current probe has a flexible substrate mounting the excitation coil, the first detection coil and the second detection coil thereon.

(10) In order to accomplish the object, an eddy current testing method for inspecting a change in characteristics of a target object using an eddy current probe, comprises: a first step of calculating a phase angle of a signal detected by the eddy current probe; and a second step of generating and outputting image data that indicates the phase angle of the detected signal in coordinates in which at least one of the position of a portion of the target object from which the signal is detected, and a time when the signal is detected from the portion, is plotted along a coordinate axis, or generating and outputting image data that indicates information based on the phase angle in the coordinates.

(11) In the eddy current testing method described in item (10), the eddy current probe has at least one excitation coil, a first detection coil and a second detection coil, the first detection coil being arranged with the excitation coil in a direction, the second detection coil being arranged with the excitation coil in another direction; the first step is performed to calculate a first phase angle of a first signal detected by the first detection coil and a second phase angle of a second signal detected by the second detection coil; and the second step is performed to generate and output a first image data that indicates the first phase angle of the first signal in coordinates in which at least of the position of a portion of the target object from which the first signal is detected, and a time when the first signal is detected from the portion, is plotted along a coordinate axis, and generate and output a second image data that indicates the second phase angle of the second signal in coordinates in which at least of the position of a portion of the target object from which the second signal is detected, and a time when the second signal is detected, is plotted along a coordinate axis.

(12) In the eddy current testing method described in item (10), the eddy current probe has at least one excitation coil, a first detection coil and a second detection coil, the first detection coil being arranged with the excitation coil in a direction, the second detection coil being arranged with the excitation coil in another direction; the first step is performed to calculate a first phase angle of a first signal detected by the first detection coil and a second phase angle of a second signal detected by the second detection coil; and the second step is performed to determine whether or not the first and second detected signals correspond to the change in the characteristics of the target object based on the relationship between the first phase angle and second phase angle, and generate and output image data that indicates an area of the signal detected and determined to correspond to the change in the characteristics of the target object in coordinates in which at least one of the position of a portion of the target object from which the signal is detected, and a time when the signal is detected from the portion, is plotted along a coordinate axis.

According to the present invention, it is possible to confirm that the change in the characteristics of the target object is detected regardless of the magnitude of the change and to specify the position of the portion from which the change in the characteristics of the target object is detected.

DESCRIPTION OF THE PREFERRED EMBODIMENTS

A first embodiment of the present invention is described below with reference to FIGS. 1 to 15.

Figure 1:
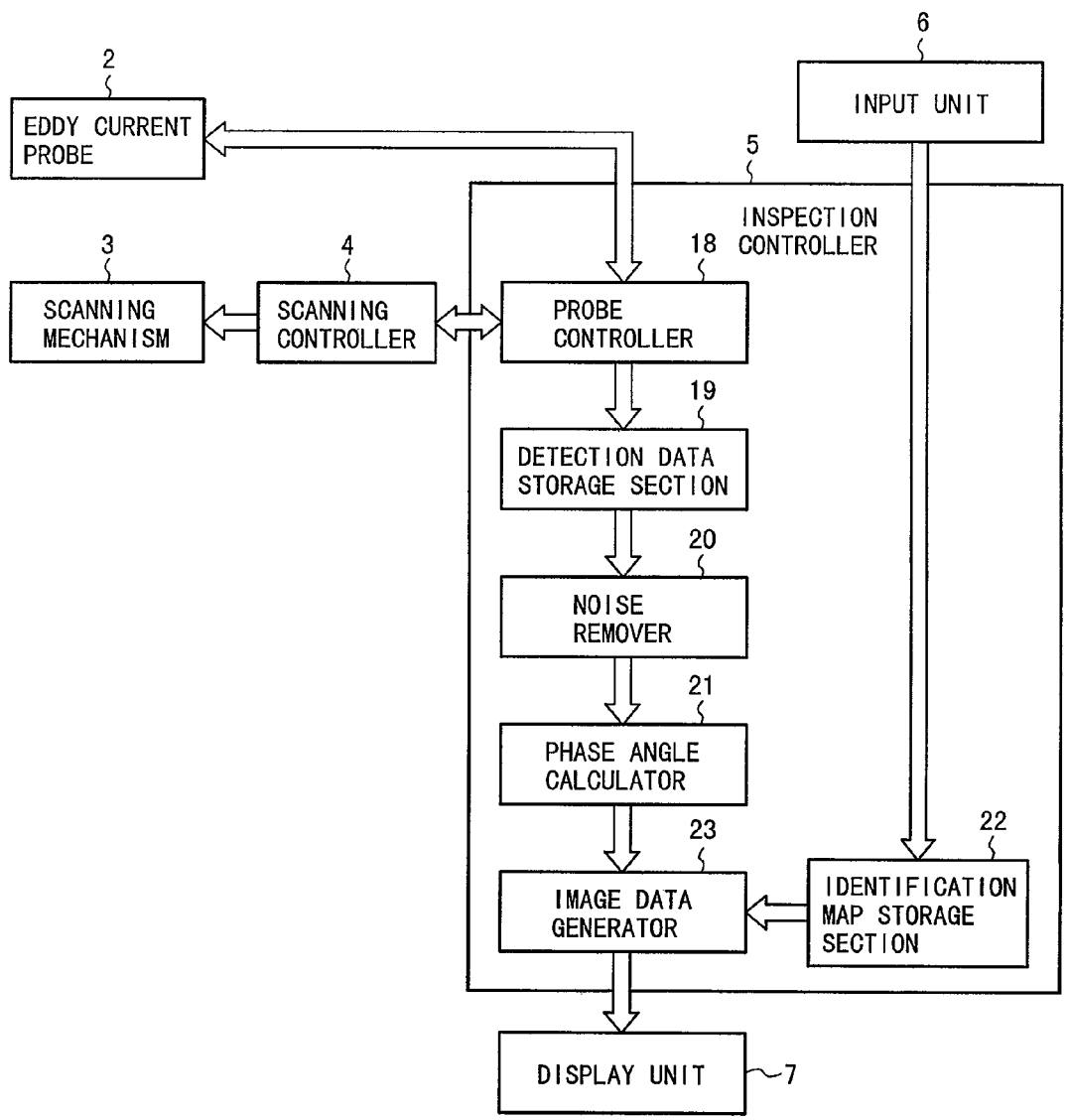
FIG. 1 is a block diagram showing the entire configuration of an eddy current testing device according to a first embodiment of the present invention.
Figure 2:
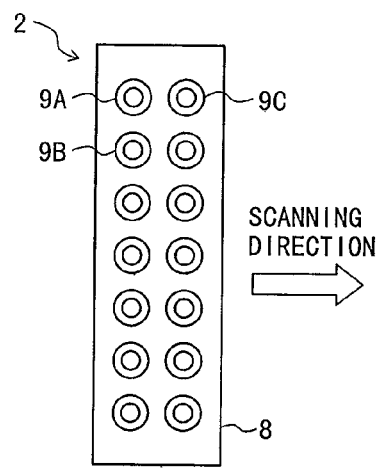
FIG. 2 is a schematic diagram showing the structure of an eddy current probe according to the first embodiment of the present invention.
Figure 3:
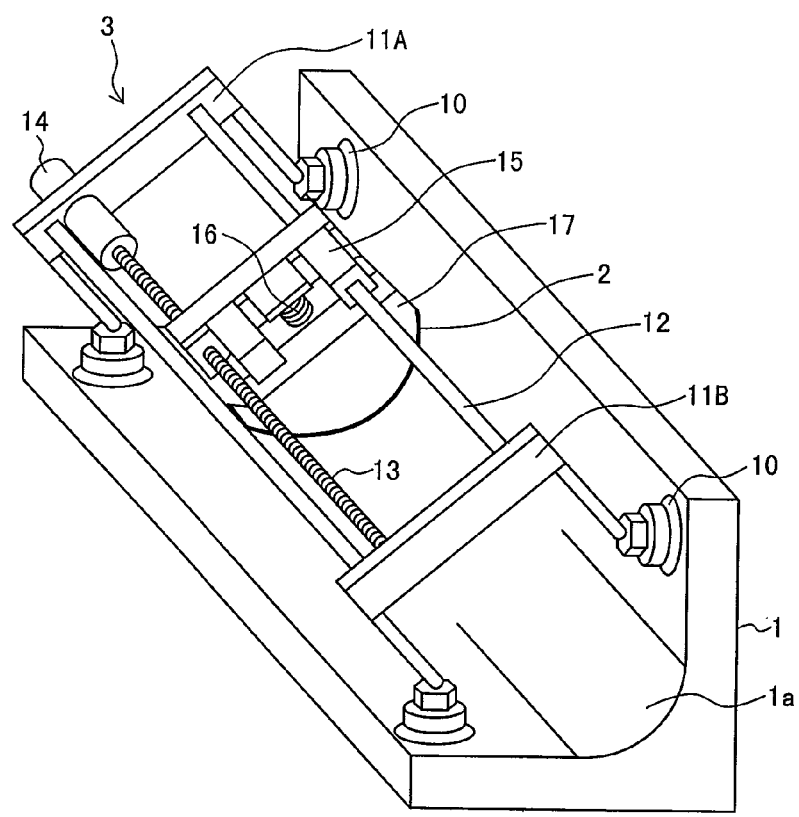
FIG. 3 is a perspective view of the structure of a scanning mechanism according to the first embodiment of the present invention.

FIG. 1 is a block diagram showing the entire configuration of an eddy current testing device according to the first embodiment of the present invention. FIG. 2 is a schematic view of the structure of an eddy current probe. FIG. 3 is a perspective view of the structure of a scanning mechanism.

The eddy current testing device is designed to inspect a bent portion 1a of a metal body 1 (shown in FIG. 3) and the like. As shown in FIGS. 1 to 3, the eddy current testing device has an eddy current probe 2, a scanning mechanism 3, a scanning controller 4, an inspection controller 5, an input unit 6 and a display unit (monitor) 7. The scanning mechanism 3 moves the eddy current probe 2 along the bent portion 1a of the metal body 1. The scanning controller 4 drives and controls the scanning mechanism 3. The inspection controller 5 is connected with the eddy current probe 2 and the scanning controller 4. The input unit 6 and the display unit 7 are connected with the inspection controller 5.

The eddy current probe 2 is a flexible multi-coil probe and has a flexible substrate 8 and a coil group. The coil group has coils squarely arranged on the flexible substrate 8 in two rows, for example. The coil group may have the coils arranged in a zigzag manner. The eddy current probe 2 has a function for switching the coils of the coil group to an excitation coil or a detection coil. For example, one of the coils arranged in a first row is an excitation coil 9A as shown in FIG. 2; a coil, which is adjacent to the excitation coil 9A and is arranged with the excitation coil 9A in a longitudinal direction (top-bottom direction in FIG. 2) of the eddy current probe 2, is a first detection coil 9B; and a coil, which is adjacent to the excitation coil 9A and is arranged with the excitation coil 9A in a lateral direction (left-right direction in FIG. 2) of the eddy current probe 2, is a second detection coil 9C. In this example, the eddy current probe 2 is capable of simultaneously inspecting a target object in two directions. In addition, the eddy current probe 2 is capable of inspecting the target object in a region extending in the longitudinal direction of the probe 2 by sequentially switching the coils arranged in the first row to excitation coils 9A. Furthermore, the scanning mechanism 3 moves the eddy current probe 2 in the lateral direction of the probe 2 to allow the eddy current probe 2 to inspect the target object in a region extending in the lateral direction of the probe 2.

The scanning mechanism 3 has a pair of frames 11A and 11B, a guide rail 12, a screw bar 13, a motor 14 and a scanner head 15. Each of the frames 11A and 11B has a fixture 10 fixed to the surface of the metal body 1 by means of a suction disk, a magnet or the like. The guide rail 12 is provided between the frames 11A and 11B and connects the frames 11A and 11B. The screw bar 13 is held by and between the frames 11A and 11B and has an axis parallel to that of the guide rail 12. The motor 14 drives and rotates the screw bar 13. The scanner head 15 is guided by the guide rail 12 and screwed to the screw bar 13. The eddy current probe 2 is attached to the scanner head 15 by means of a pressing spring 16 and an elastic member 17. The eddy current probe 2 is pressed toward the bent portion 1a of the metal body 1 by the pressing spring 16. The motor 14 is driven by a drive current signal transmitted by the scanning controller 4 to rotate the screw bar 13. When the screw bar 13 rotates, the scanner head 15 and the eddy current probe 2 moves in the direction (upper left-lower right direction in FIG. 3, or lateral direction of the probe) of the axis of the screw bar 13 (or in the direction of the axis of the guide rail 12).

The inspection controller 5 has a probe controller 18, a detection data storage section 19, a noise remover 20, a phase angle calculator 21, an identification map storage section 22, and an image data generator 23.

The probe controller 18 outputs a command signal to the scanning controller 4. The scanning controller 4 drives and controls the scanning mechanism 3 based on the command signal output by the probe controller 18. In addition, the probe controller 18 receives a signal from the scanning controller 4 and calculates the amount of a movement of the eddy current probe 2 (or calculates an area scanned by the eddy current probe 2) based on the signal received from the scanning controller 4. The probe controller 18 performs control to sequentially switch the coils arranged in the first row to the excitation coils 9A and receives a signal detected by a first detection coil 9B and a signal detected by a second detection coil 9C. The probe controller 18 identifies the positions (in the lateral and longitudinal directions of the probe) of portions (from which the signals are detected) of the target object based on the area scanned by the eddy current probe 2 and on the position of the excitation coil 9A. The position of a portion (of the target object) from which a signal is detected is hereinafter also called a detection position. The probe controller 18 converts the signal detected by the first detection coil 9B into an X component voltage and a Y component voltage. The probe controller 18 outputs information on the relationship between the X and Y component voltages and the detection position to the detection data storage section 19. Similarly, the probe controller 18 converts the signal detected by the second detection coil 9C into an X component voltage and a Y component voltage and outputs information on the relationship between the X and Y component voltages and the detection position to the detection data storage section 19.

The detection data storage section 19 accumulates, as detection data, the relationship between the X and Y component voltages obtained from the first detection coil 9B and the detection position, and accumulates, as detection data, the relationship between the X and Y component voltages obtained from the second detection coil 9C and the detection position. The detection data obtained from the first detection coil 9B is used as an example and is described below with reference to FIGS. 4A and 4B.

Figure 4A:
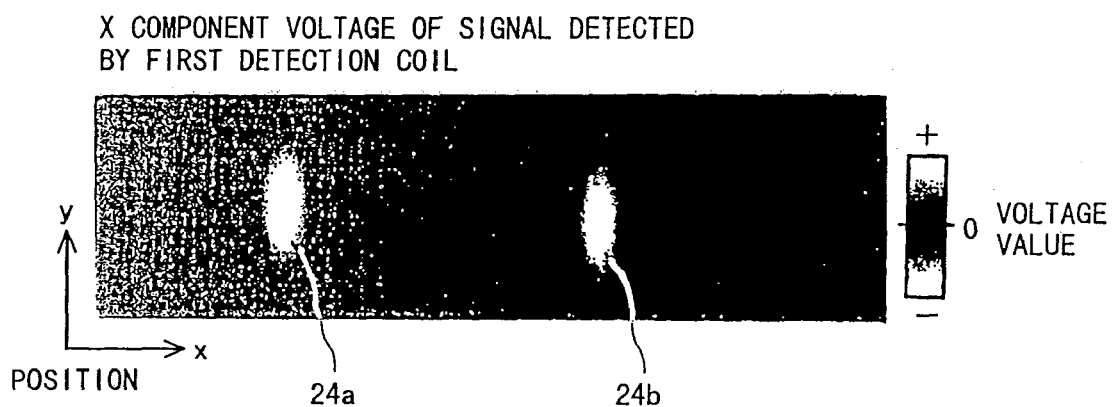
FIGS. 4A and 4B are diagrams showing an example of detection data stored in a detection data storage section provided in an inspection controller according to the first embodiment of the present invention.
Figure 4B:
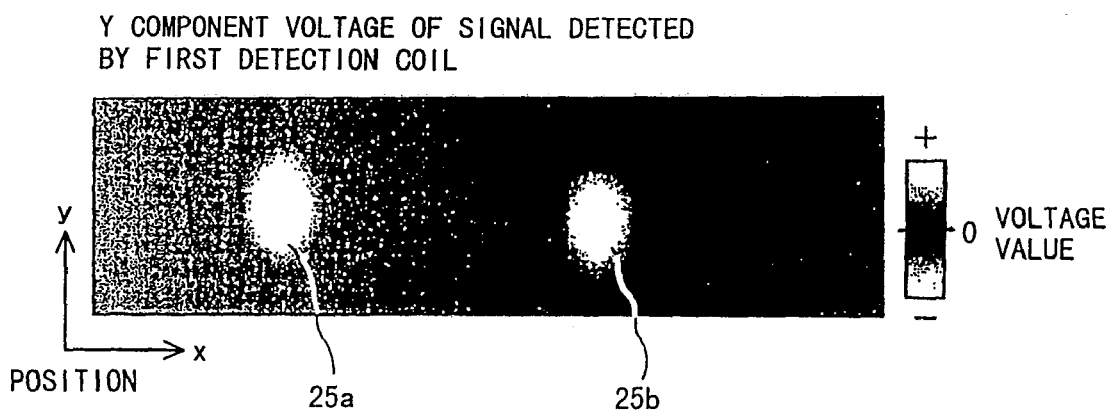

FIG. 4A shows the detection data indicative of the X component voltage, while FIG. 4B shows the detection data indicative of the Y component voltage. The detection data shown in FIGS. 4A and 4B is represented in two dimensional coordinates. In the two dimensional coordinates, the position of the portion of the target object (from which the signal is detected) in the lateral direction of the probe is plotted along an X axis, and the position of the portion of the target object (from which the signal is detected) in the longitudinal direction of the probe is plotted along a Y axis. In addition, the detection data shown in FIGS. 4A and 4B is represented as voltage image data. That is, voltage values of the detection data shown in FIGS. 4A and 4B are indicated by means of chromaticity (or brightness) of pixels. Voltage indicator signals 24a and 24b appear in the detection data indicative of the X component voltage, and a noise signal (electrical noise) specific to the device appears in a region other than regions in which the voltage indicator signals 24a and 24b appear. Voltage indicator signals 25a and 25b, which are respectively related to the voltage indicator signals 24a and 24b, appear in the detection data indicative of the Y component voltage. A noise signal (electrical noise) specific to the device appears in a region other than regions in which the voltage indicator signals 25a and 25b appear.

The noise remover 20 (described later) removes a noise signal from each of the following data: the detection data indicative of the X component voltage obtained from the first detection coil 9B; the detection data indicative of the Y component voltage obtained from the first detection coil 9B; the detection data indicative of the X component voltage obtained from the second detection coil 9C; and the detection data indicative of the Y component voltage obtained from the second detection coil 9C.

After the noise signal is removed from the detection data indicative of the X component voltage obtained from the first detection coil 9B and from the detection data indicative of the Y component voltage obtained from the first detection coil 9B, the phase angle calculator 21 performs predetermined arithmetic processing on the detection data indicative of the X component voltage obtained from the first detection coil 9B and on the detection data indicative of the Y component voltage obtained from the first detection coil 9B to calculate a phase angle of the signal detected by the first detection coil 9B for each detection position. The phase angle calculator 21 then outputs data on the calculated phase angle to the image data generator 23. Similarly, after the noise signal is removed from the detection data indicative of the X component voltage obtained from the second detection coil 9C and from the detection data indicative of the Y component voltage obtained from the second detection coil 9C, the phase angle calculator 21 performs predetermined arithmetic processing on the detection data indicative of the X component voltage obtained from the second detection coil 9C and on the detection data indicative of the Y component voltage obtained from the second detection coil 9C to calculate a phase angle of the signal detected by the second detection coil 9C for each detection position. The phase angle calculator 21 then outputs data on the calculated phase angle to the image data generator 23.

Figure 5A:
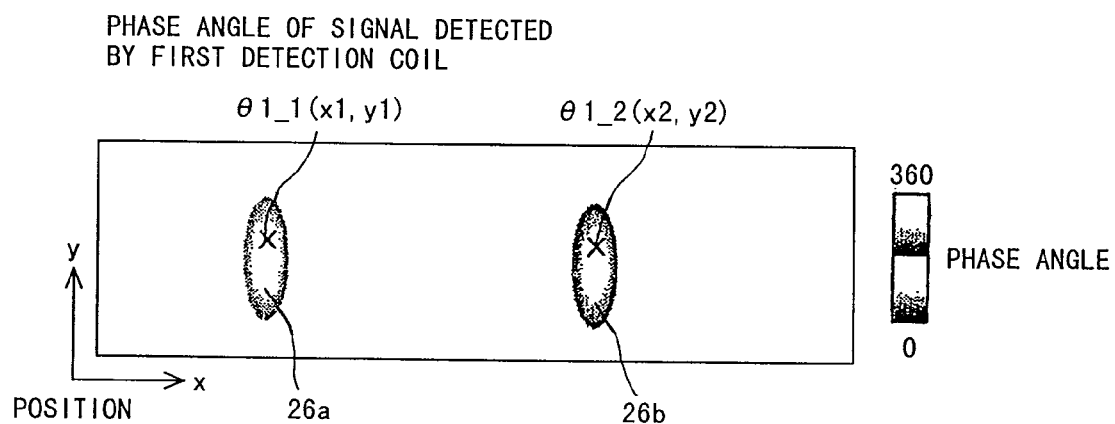
FIGS. 5A and 5B are diagrams showing an example of phase angle image data generated by an image data generator provided in the inspection controller according to the first embodiment of the present invention.
Figure 5B:
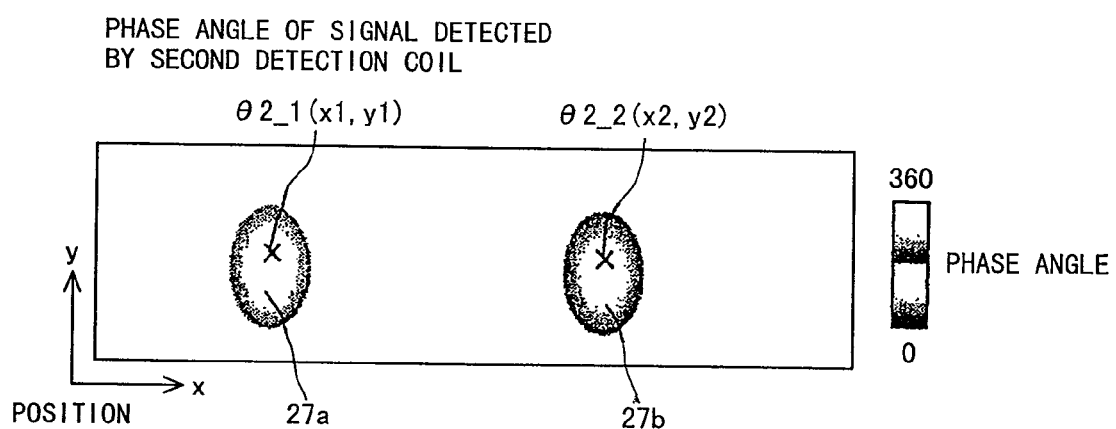

The image data generator 23 has a first function (means for generating phase angle image data) for generating phase angle image data (refer to FIG. 5A). The phase angle image data indicates the phase angle of the signal detected by the first detection coil 9B by means of chromaticity (or brightness) of the pixels in two dimensional coordinates. In the two dimensional coordinates, the position of the portion of the target object (from which the signal is detected) in the lateral direction of the probe is plotted along an X axis and the position of the portion of the target object (from which the signal is detected) in the longitudinal direction of the probe is plotted along a Y axis. Similarly, the image data generator 23 generates phase angle image data (refer to FIG. 5B) that indicates the phase angle of the signal detected by the second detection coil 9C. A phase angle indicator signal 26a, which is the result of a calculation based on the voltage indicator signals 24a and 25a, appears in the image data that indicates the phase angle of the signal detected by the first detection coil 9B. Also, a phase angle indicator signal 26b, which is the result of a calculation based on the voltage indicator signals 24b and 25b, appears in the image data that indicates the phase angle of the signal detected by the first detection coil 9B. In addition, phase angle indicator signals 27a and 27b, which are respectively related to detection positions from which the phase angle indicator signals 26a and 26b are obtained, appear in the image data that indicates the phase angle of the signal detected by the second detection coil 9C.

Figure 6A:
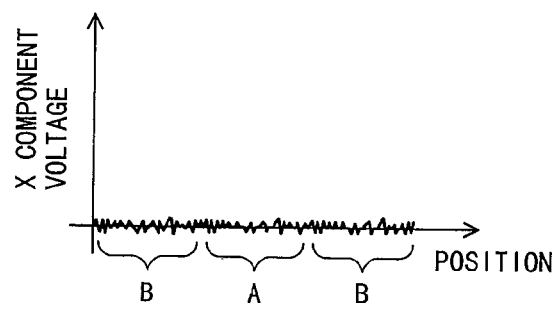
FIGS. 6A to 6D are graphs to explain a noise signal included in detection data.
Figure 6B:
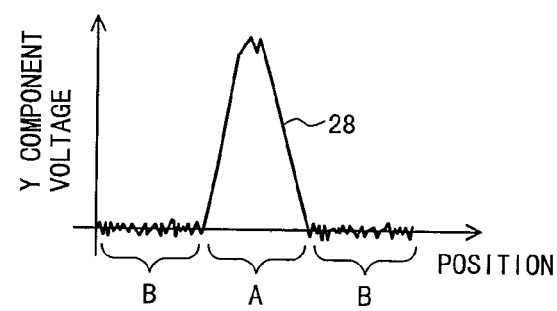
Figure 6C:
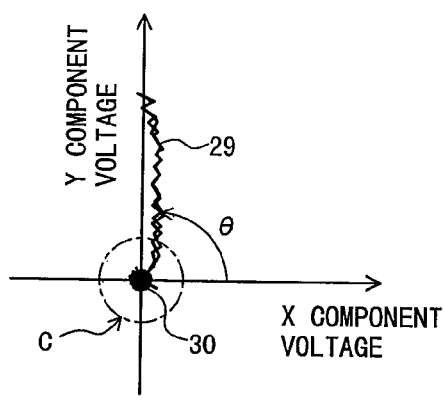
Figure 6D:
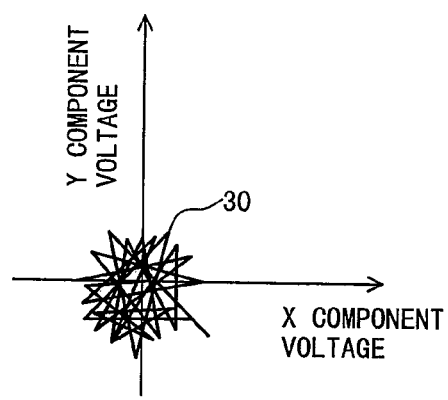
Figure 7:
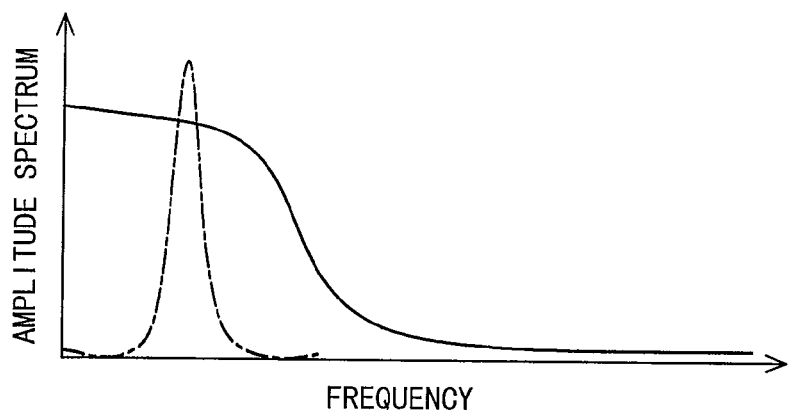
FIG. 7 is a diagram showing characteristics of a noise signal remover provided in the inspection controller according to the first embodiment of the present invention.
Figure 8:
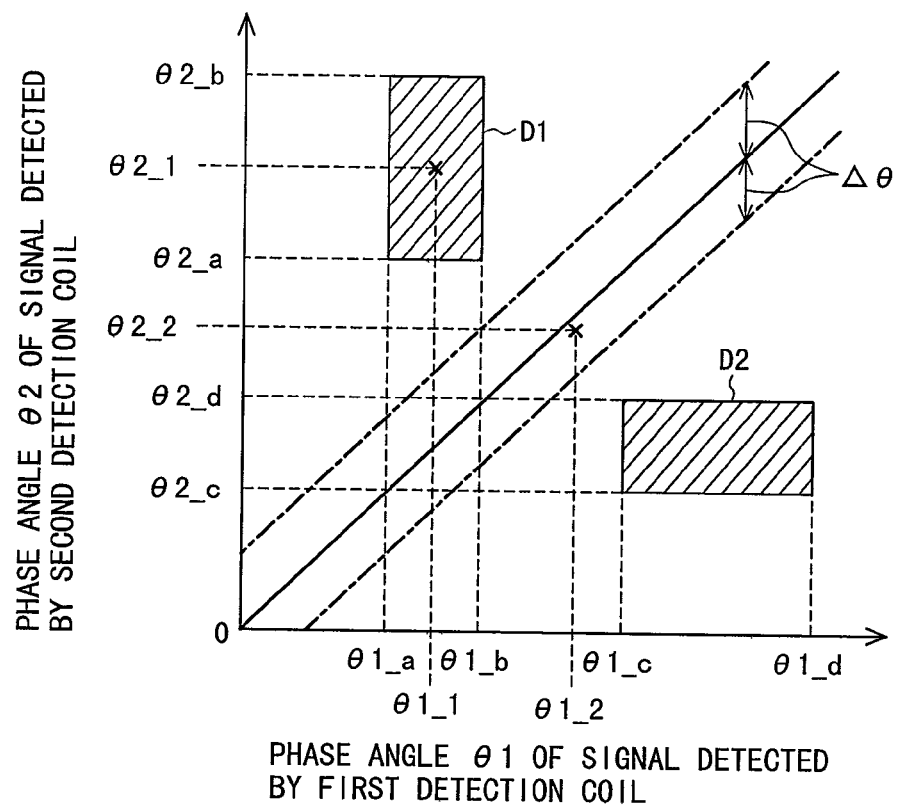
FIG. 8 is a diagram showing an example of an identification map stored in an identification map storage section provided in the inspection controller according to the first embodiment of the present invention.

Processing for removing a noise signal by means of the noise remover 20 is described below in detail. FIGS. 6A and 6B are graphs each showing examples of the X and Y component voltages included in the detection signal, respectively. In the graphs, the detection position is plotted along an abscissa axis, and the voltage is plotted along an ordinate axis. In the graphs shown in FIGS. 6A and 6B, a symbol A indicates an area in which a voltage indicator signal 28 is present, and a symbol B indicates an area in which the voltage indicator signal 28 is not present. A noise signal having extremely small amplitude (in other words, a noise signal having extremely small X and Y component voltages) appears in the area B. FIG. 6C shows a Lissajous diagram of the graphs shown in FIGS. 6A and 6B. In the Lissajous diagram, the X component voltage is plotted along an abscissa axis, and the Y component voltage is plotted along an ordinate axis. In the Lissajous diagram shown in FIG. 6C, a Lissajous pattern 29 corresponding to the voltage indicator signal 28 appears to allow the phase angle θ to be evaluated. In this case, if the processing for removing a noise signal is not performed before the Lissajous diagram is plotted, a Lissajous pattern 30 corresponding to a noise signal appears. The Lissajous pattern 30 is shown in FIG. 6D, which is an enlarged view of a part indicated by a symbol C shown in FIG. 6C. The Lissajous pattern 30 has various values to cause the phase angle to be nonuniform. Therefore, if the processing for removing a noise signal is not performed before the Lissajous diagram is plotted, it is difficult to discriminate between the phase angle indicator signal and a noise signal from the image data on the phase angle. This results in a reduction in accuracy of detection of the phase angle indicator signal.

To avoid this problem, the noise remover 20 removes a noise signal from the following data: the detection data indicative of the X component voltage obtained from the first detection coil 9B; the detection data indicative of the Y component voltage obtained from the first detection coil 9B; the detection data indicative of the X component voltage obtained from the second detection coil 9C; and the detection data indicative of the Y component voltage obtained from the second detection coil 9C, in the present embodiment. Specifically, the noise remover 20 uses a frequency filter to remove a noise signal having a frequency within a preset predetermined frequency band (specifically, to remove a noise signal having a frequency other than frequencies within a test frequency band) from the aforementioned detection data. The frequency filter includes a low pass filter, a high pass filter, or a band pass filter, or uses the combination of the filters based on characteristics of the noise signal and on responsiveness of the detected signal. For example, when an amplitude spectrum of a frequency band close to the test frequency band is relatively large as represented by a solid line (indicative of a characteristic of a noise signal obtained in advance by testing, inspection or the like) shown in FIG. 7, the band pass filter is used to extract a test frequency component as represented by a broken line shown in FIG. 7. Since the processing for removing a noise signal is performed in this way in advance, a noise signal almost does not appear in the phase angle image data generated by the image data generator 23. This makes it possible to improve the accuracy of the detection of the phase angle indicator signal.

The image data generator 23 has a second function (means for determining a flaw signal) for performing predetermined arithmetic processing on the image data indicative of the phase angle of the signal detected by the first detection coil 9B and on the image data indicative of the phase angle of the signal detected by the second detection coil 9C to determine whether or not the detected signals (for example, the phase angle indicator signals 26a, 27a and the phase angle indicator signals 26b, 27b) correspond to flaw signals. Specifically, the identification map storage section 22 has an identification map stored therein (refer to FIG. 8). The identification map includes preset predetermined standard areas D1 and D2 and is represented in coordinates in which the phase angle of the signal detected by the first detection coil 9B is plotted along an abscissa axis and the phase angle of the signal detected by the second detection coil 9C is plotted along an ordinate axis. Before data on the standard area D1 and data on the standard area D2 are entered, a lift-off signal (described later) and a bending signal (described later) are evaluated. The data on the standard area D1 and the data on the standard area D2 are entered based on the evaluation result by means of the input unit 6. The image data generator 23 then reads the identification map from the identification map storage section 22 and determines whether or not the phase angle of the signal detected by the first detection coil 9B and the phase angle of the signal detected by the second detection coil 9C are included in the standard areas D1 and D2 for each detection position to determine whether or not the detected signals correspond to flaw signals. The processing for the determination is described below in detail.

Figure 9A:
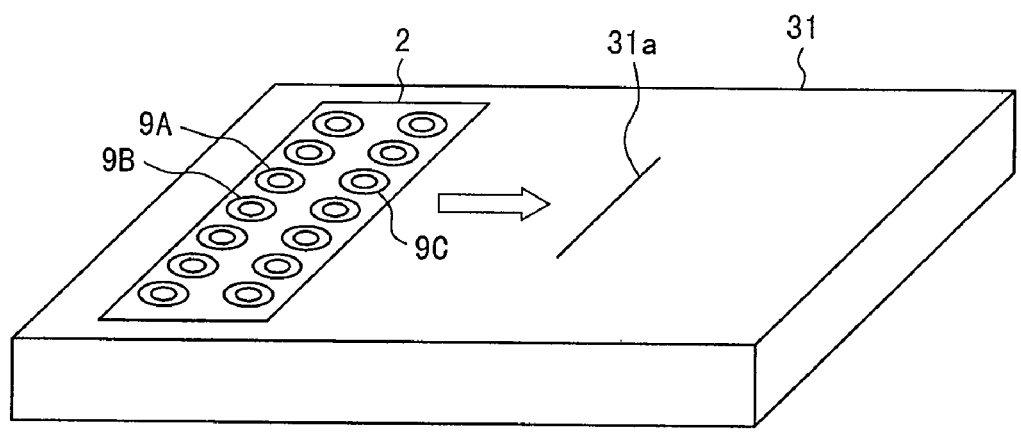
FIGS. 9A and 9B are diagrams to explain a phase angle in the case where a flaw signal is detected.
Figure 9B:
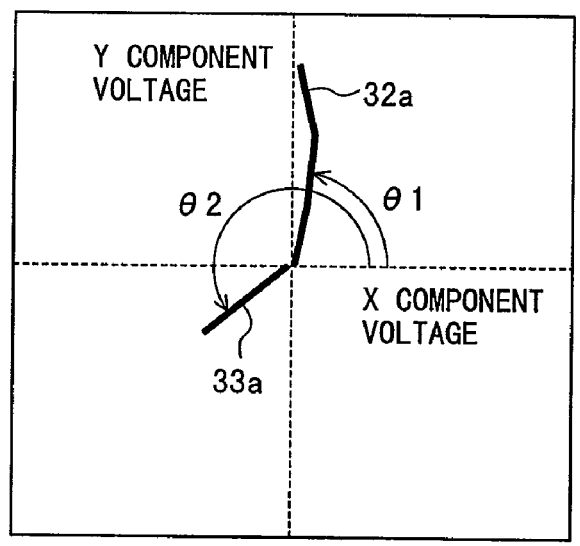

Referring to FIG. 9A, reference numeral 31 denotes the target object, and reference numeral 31a denotes a crack of the target object 31. For example, when the crack 31a of the target object 31 extends in the longitudinal direction of the probe 2, the direction in which the excitation coil 9A and first detection coil 9B of the eddy current probe 2 are arranged is nearly parallel to the direction in which the crack 31a extends. When the signal detected by the first detection coil 9B is plotted in a Lissajous diagram shown in FIG. 9B, a Lissajous pattern 32a appears in the Lissajous diagram, and the phase angle θ1 (of the signal detected by the first detection coil 9B) of 90 degrees can be obtained based on the Lissajous pattern 32a. In addition, the direction in which the excitation coil 9A and second detection coil 9C of the eddy current probe 2 are arranged is nearly perpendicular to the direction in which the crack 31a extends. When the signal detected by the second detection coil 9C is plotted in the Lissajous diagram shown in FIG. 9B, a Lissajous pattern 33a appears in the Lissajous diagram, and the phase angle θ2 (of the signal detected by the second detection coil 9C) of 230 degrees can be obtained based on the Lissajous pattern 33a. A flaw signal corresponding to the crack 31a is included in an area defined by the expression of $\theta1\_a \leq \theta1 \leq \theta1\_b$ (for example, $80° \leq \theta1 \leq 100°$) and the expression of $\theta2\_a \leq \theta2 \leq \theta2\_b$ (for example, $180° \leq \theta2 \leq 260°$). That is, the flaw signal corresponding to the crack 31a is included in the predetermined standard area D1 on the identification map.

On the other hand, when the target object has a crack (not shown) extending in the lateral direction of the probe 2, the direction in which the excitation coil 9A and the first detection coil 9B are arranged is nearly perpendicular to the direction in which the crack extends. The direction in which the excitation coil 9A and the second detection coil 9C are arranged is nearly parallel to the direction in which the crack extends. In this case, the phase angle θ1 of the signal detected by the first detection coil 9B is 230 degrees. The phase angle θ2 of the signal detected by the second detection coil 9C is 90 degrees. A flaw signal corresponding to the crack extending in the lateral direction of the probe 2 is included in an area defined by the expression of $\theta1\_c \leq \theta1 \leq \theta1\_d$ (for example, $180° \leq \theta1 \leq 260°$) and the expression of $\theta2\_c \leq \theta2 \leq \theta2\_d$ (for example, $80° \leq \theta2 \leq 100°$). That is, the flaw signal corresponding to the crack extending in the lateral direction of the probe 2 is included in the predetermined standard area D2 on the identification map.

Figure 10A:
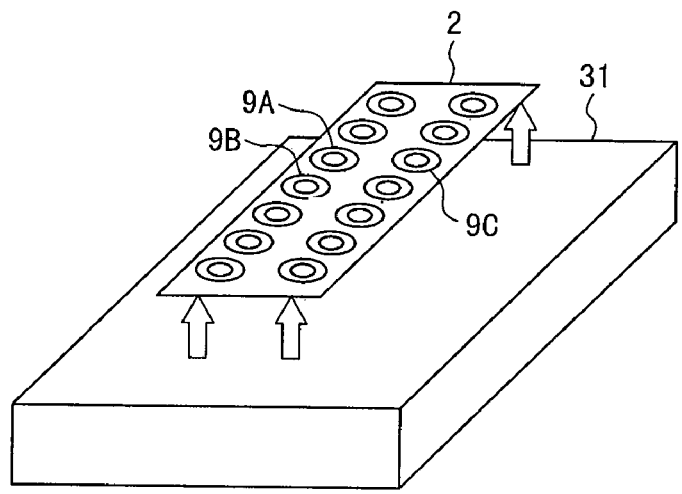
FIGS. 10A and 10B are diagrams to explain a phase angle in the case where a lift-off signal is detected.
Figure 10B:
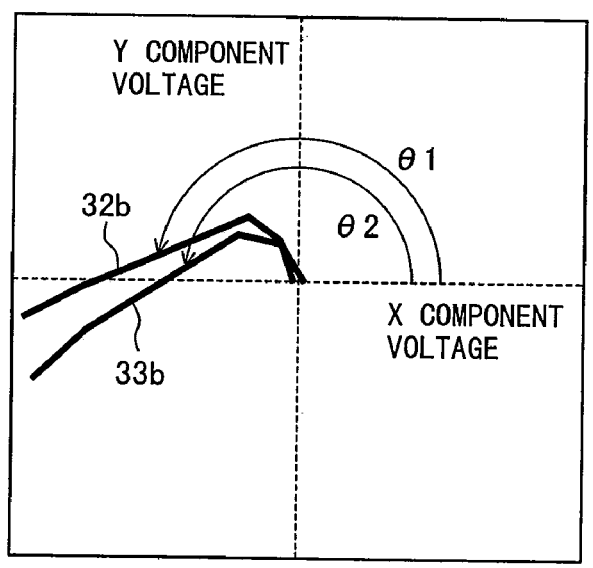

Furthermore, since the eddy current probe 2 is a flexible multi-coil probe, a lift-off signal and a bending signal (detected from a bent portion of a target object) are detected depending on the state of the surface of the target object and on the shape of the target object. For example, when the eddy current probe 2 floats above the target object 31 as shown in FIG. 10A, a lift-off signal is detected. When the signal detected by the first detection coil 9B and the signal detected by the second detection coil 9C are plotted in the Lissajous diagram as shown in FIG. 10B, Lissajous patterns 32b and 33b appear in the Lissajous diagram. In this case, the phase angles θ1 and θ2 of the detected signals are close to 180 degrees and close to each other. The lift-off signal obtained in this case is included in an area surrounded by alternate long and short dash lines shown in FIG. 8, i.e., is included in an area defined by the expression of $|\theta2-\theta1| \leq \Delta\theta$ (for example, $\Delta\theta=20°$). That is, the lift-off signal is not included in the standard areas D1 and D2.

Figure 11A:
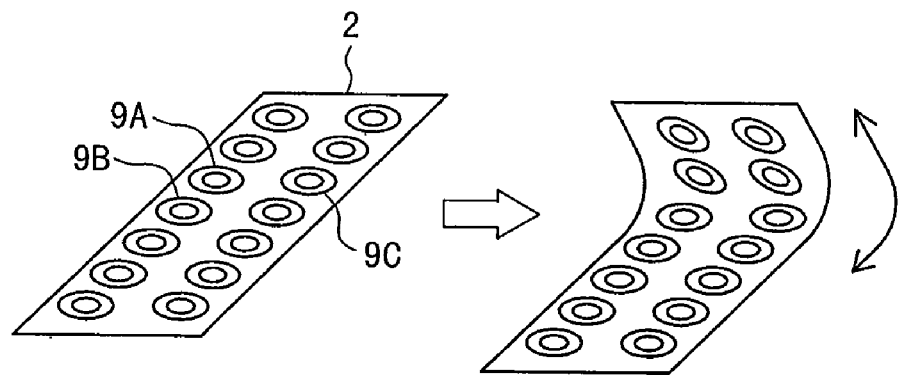
FIGS. 11A and 11B are diagrams to explain a phase angle in the case where a bending signal is detected.
Figure 11B:
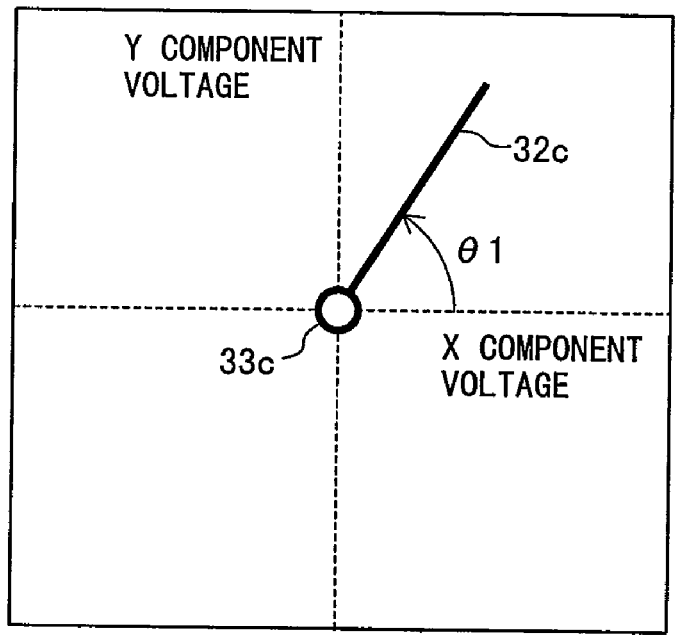

When the eddy current probe 2 is bent based on the bent portion of the target object as shown in FIG. 11A, a bending signal is detected by the eddy current probe 2. Specifically, when the eddy current probe 2 is bent in the longitudinal direction of the probe 2, a distance between the excitation coil 9A and the first detection coil 9B is changed. In this case, however, the distance between the excitation coil 9A and the second detection coil 9C is not changed. When the signal detected by the first detection coil 9B is plotted in the Lissajous diagram as shown in FIG. 11B, a Lissajous pattern 32c appears in the Lissajous diagram. The phase angle θ1 can be obtained based on the Lissajous pattern 32c. When the signal detected by the second detection coil 9C is plotted in the Lissajous diagram, a Lissajous pattern 33c (nearly corresponding to a noise signal) appears in the Lissajous diagram. However, the phase angle cannot be obtained based on the Lissajous pattern 33c. This bending signal is plotted near the abscissa axis ($\theta2=0°$) on the identification map and is not included in the standard areas D1 and D2.

Since the image data generator 23 determines whether or not the phase angle of the signal detected by the first detection coil 9B and the phase angle of the signal detected by the second detection coil 9C are included in the standard areas D1 and D2, the flaw signal and other signals (lift-off signal and bending signal) can be distinguished. For example, a point obtained by combining a phase angle $\theta1\_1$ (x1, y1) (shown in FIG. 5A) of the signal detected by the first detection coil 9B at a detection position (x1, y1) with a phase angle $\theta2\_1$ (x1, y1) (shown in FIG. 5B) of the signal detected by the second detection coil 9C at the detection position (x1, y1) is included in the predetermined standard area D1 on the identification map. The image data generator 23 determines that the signal detected from the detection position (x1, y1) corresponds to a flaw signal. In addition, a point obtained by combining a phase angle $\theta1\_2$ (x2, y2) (shown in FIG. 5A) of the signal detected by the first detection coil 9B at a detection position (x2, y2) with a phase angle $\theta2\_2$ (x2, y2) (shown in FIG. 5B) of the signal detected by the second detection coil 9C at the detection position (x2, y2) is not included in the predetermined standard areas D1 and D2 on the identification map. The image data generator 23 determines that the signal detected from the detection position (x2, y2) does not correspond to a flaw signal.

Figure 12:
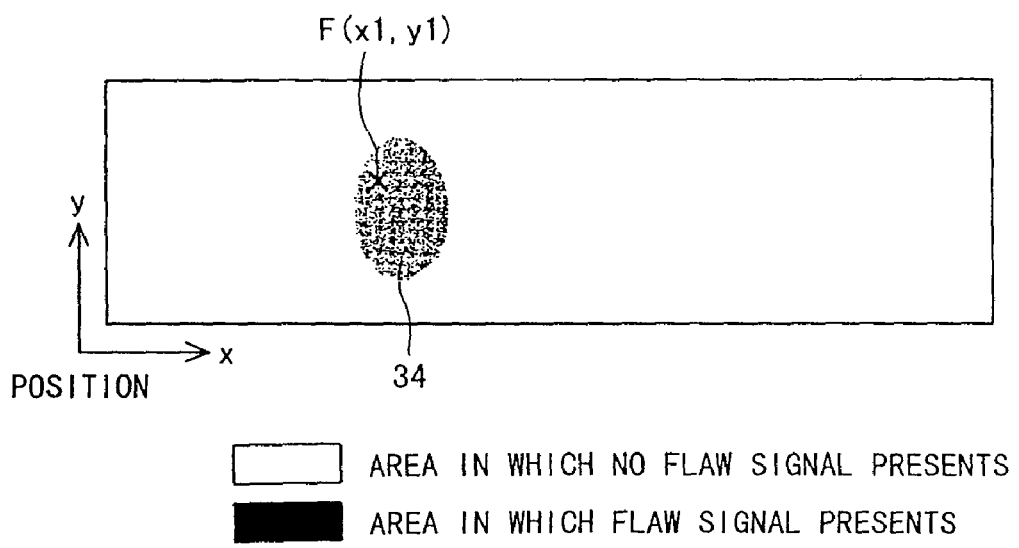
FIG. 12 is a diagram showing an example of flaw identification image data generated by the image data generator provided in the inspection controller according to the first embodiment of the present invention.

The image data generator 23 has a third function (means for generating flaw identification image data) for generating flaw identification image data (refer to FIG. 12). The flaw identification image data indicates an area 34 of the signal detected and determined to correspond to a flaw signal by the image data generator 23. The area 34 is represented in two dimensional coordinates in which the position of a portion of the target object (from which the signal is detected) in the lateral direction of the probe is plotted along as an X axis and the position of the portion of the target object (from which the signal is detected) in the longitudinal direction of the probe is plotted along as a Y axis. The image data generator 23 outputs the flaw identification image data to the display unit 7. The display unit 7 then displays an image included in the flaw identification image data.

An effect of the thus configured eddy current testing device according to the present embodiment is described below based on the result of inspection of a sample.

Figure 13:
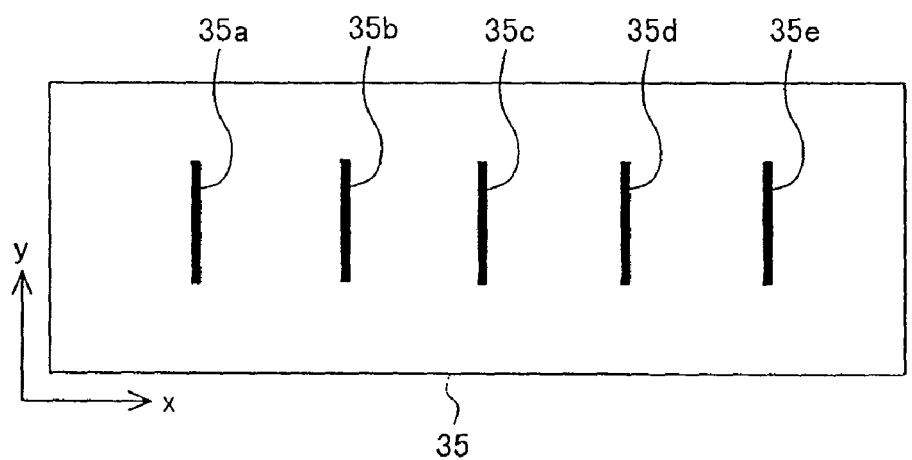
FIG. 13 is a plan view of the structure of a sample.

FIG. 13 is a plan view of the structure of a sample 35. The sample 35 has a flat plate shape. The sample 35 has artificial cracks 35a to 35e artificially formed by electric discharge machining or the like. The artificial cracks 35a to 35e extend in the same direction. The depth of the artificial crack 35a is larger than that of the artificial crack 35b. The depth of the artificial crack 35b is larger than that of the artificial crack 35c. The depth of the artificial crack 35c is larger than that of the artificial crack 35d. The depth of the artificial crack 35d is larger than that of the artificial crack 35e. The eddy current probe 2 is placed to ensure that a longitudinal direction (top-bottom direction of FIG. 13) of the artificial cracks 35a to 35e is nearly parallel to the longitudinal direction of the eddy current probe 2 (or is nearly perpendicular to the lateral direction of the eddy current probe 2). The eddy current probe 2 moves in the lateral direction (left-right direction of FIG. 13) of the eddy current probe 2 to inspect the sample 35.

Figure 14A:
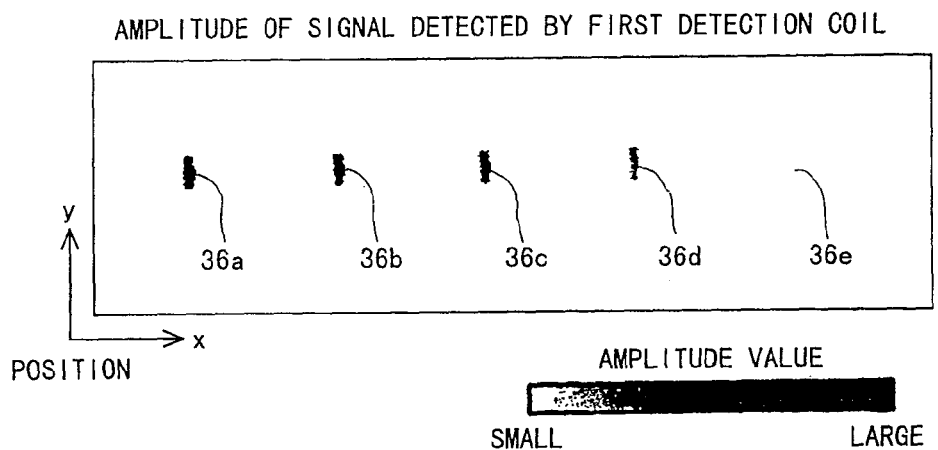
FIGS. 14A and 14B are diagrams showing images that indicate a distribution of amplitude and are displayed as the result of an inspection of the sample in a comparative example.
Figure 14B:
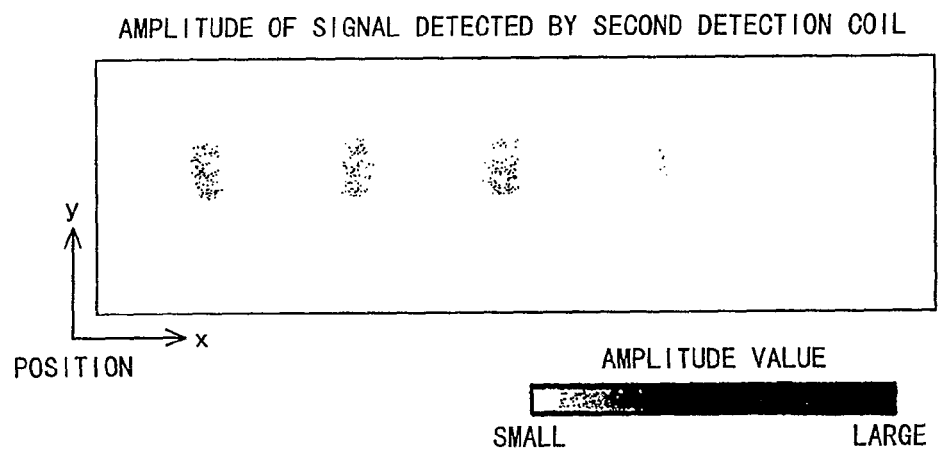

As shown in FIGS. 14A and 14B, it is assumed that an image indicative of a distribution of amplitude of a signal detected by the first detection coil 9B is displayed as the result of the inspection, and that an image indicative of a distribution of amplitude of a signal detected by the second detection coil 9C is displayed as the result of the inspection. The images shown in FIGS. 14A and 14B are displayed in two dimensional coordinates in which the position of a portion of the sample 35 (from which the signal is detected) in the lateral direction of the probe 2 is plotted along an X axis and the position of the portion of the sample 35 (from which the signal is detected) in the longitudinal direction of the probe 2 is plotted along a Y axis. The amplitude of the detected signal is indicated by grayscale shading based on the depths of the cracks 35a to 35e. Amplitude indicator signals 36a to 36d, which respectively correspond to the artificial cracks 35a to 35d having relatively large depths, remarkably appear in the image indicative of the distribution of the amplitude of the signal detected by the first detection coil 9B. It is possible to confirm that the artificial cracks 35a to 35d are detected and to specify the positions of portions of the sample 35 from which the artificial cracks 35a to 35d are detected. An amplitude indicator signal 36e corresponding to the artificial crack 35e having the smallest depth does not remarkably appear due to a lift-off signal, a bending signal and the like. It is difficult to accurately determine whether or not the artificial crack 35e is detected.

Figure 15:
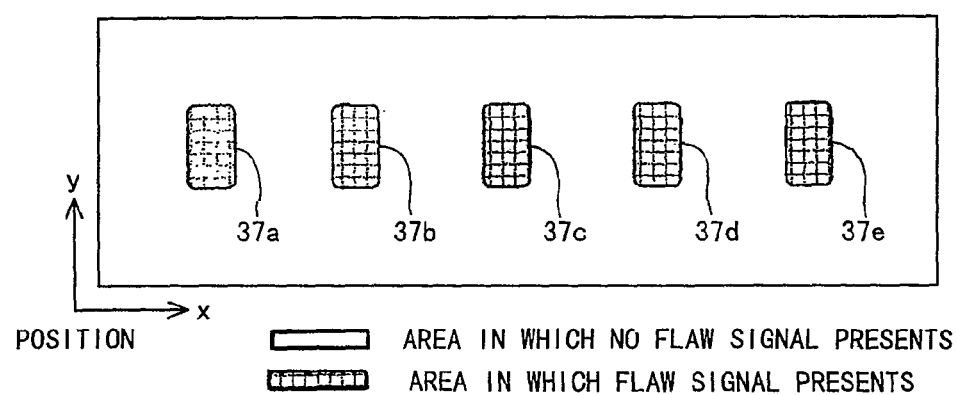
FIG. 15 is a diagram showing a flaw identification distribution image displayed as the result of an inspection of the sample, according to the first embodiment of the present invention.

On the other hand, the inspection controller 5 according to the present embodiment generates phase angle image data that indicates the phase angle of the signal detected by the first detection coil 9B in the two dimensional coordinates. In the two dimensional coordinates, the position of the portion of the sample 35 (from which the signal is detected) in the lateral direction of the probe 2 is plotted along the X axis and the position of the portion of the sample 35 (from which the signal is detected) in the longitudinal direction of the probe 2 is plotted along the Y axis. Similarly, the inspection controller 5 generates phase angle image data that indicates the phase angle of the signal detected by the second detection coil 9C in the two dimensional coordinates. According to the present embodiment, the phase angle of the detected signal depends on the shape of a crack, the direction of extension of the crack and the like, regardless of the depth of the crack. Therefore, the phase angle indicator signal is not hidden by a lift-off signal, a bending signal and the like. In addition, the inspection controller 5 determines whether or not the detected signal corresponds to a flaw signal by plotting the image data indicative of the phase angle of the signal detected by the first detection coil 9B and the image data indicative of the phase angle of the signal detected by the second detection coil 9C on the identification map. The inspection controller 5 then generates flaw identification image data that indicates, in the two dimensional coordinates, an area of the signal detected and determined to correspond to a flaw signal. In the two dimensional coordinates, the position of a portion of the sample 35 (from which the signal is detected) in the lateral direction of the probe 2 is plotted along the X axis and the position of the portion of the sample 35 (from which the signal is detected) in the longitudinal direction of the probe 2 is plotted along the Y axis. The inspection controller 5 then outputs the generated flaw identification image data to the display unit 7. The display unit 7 displays an image (flaw identification distribution image) included in the flaw identification image data. As shown in FIG. 15, areas 37a to 37e corresponding to the artificial cracks 35a to 35e clearly appear in the image displayed in the aforementioned way by the display unit 7. It is possible to easily confirm that the artificial cracks 35a to 35e are detected and to specify the positions of the portions (of the sample) from which the artificial cracks 35a to 35e are detected. Furthermore, it is possible to reduce efforts and working time (of an inspector) to determine whether or not a detected signal corresponds to a flaw signal.

A second embodiment of the present invention is described below with reference to FIGS. 16 to 20. The second embodiment is to differentiate between a signal detected from a certain detection position (or at a certain time) and a signal detected from a detection position close to the certain detection position (or at a time close to the certain time) and to perform arithmetic processing on the differentiated detection signals.

Figure 16:
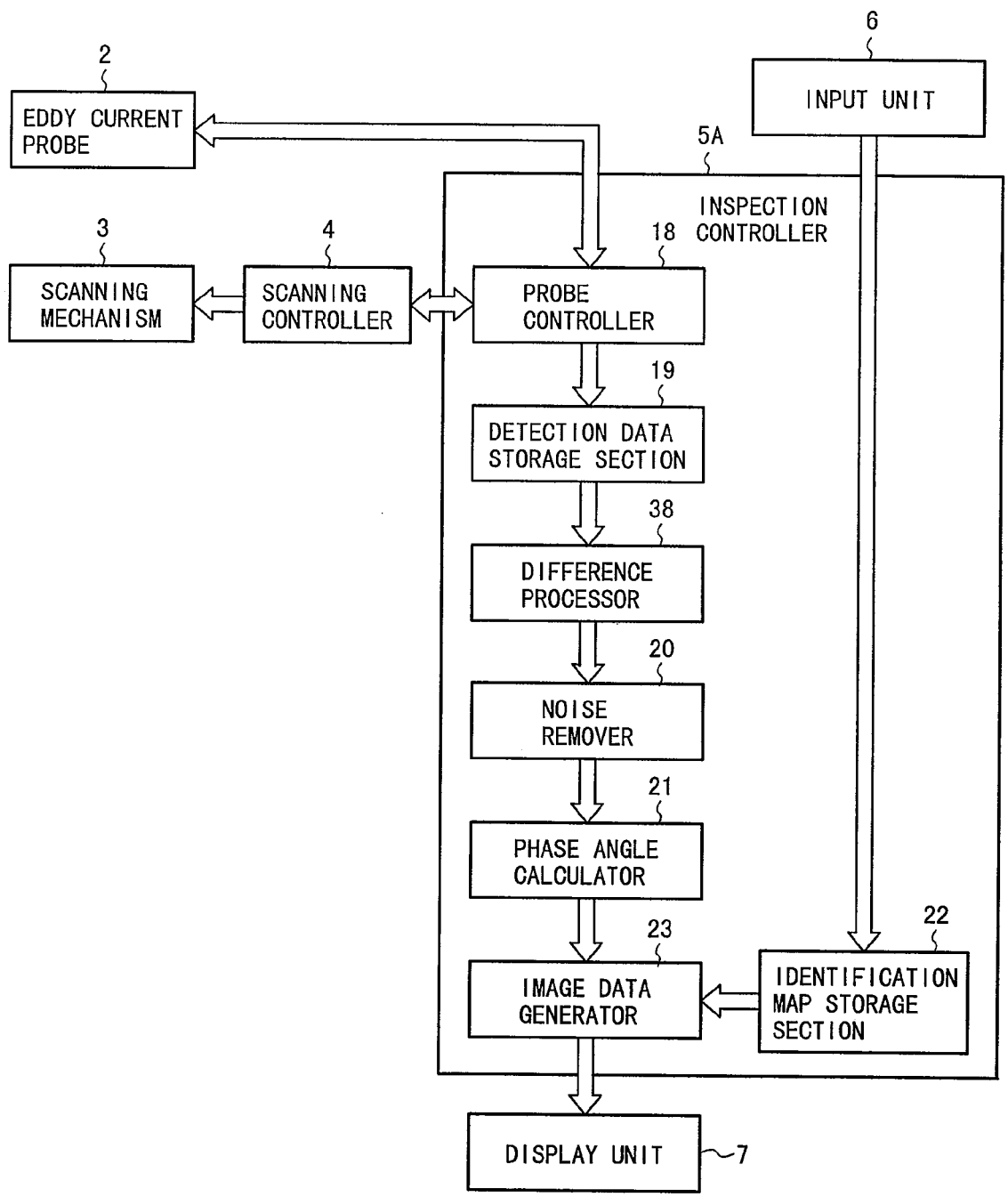
FIG. 16 is a block diagram showing the entire configuration of an eddy current testing device according to a second embodiment of the present invention.
Figure 17A:
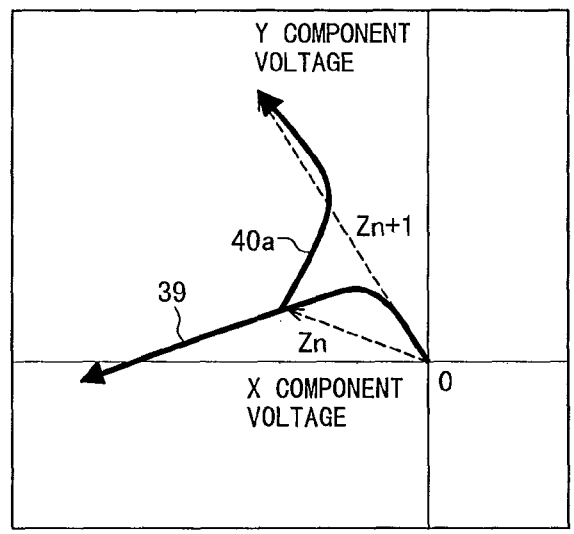
FIGS. 17A to 17C are diagrams to explain differentiated detection signals according to the second embodiment of the present invention.
Figure 17B:
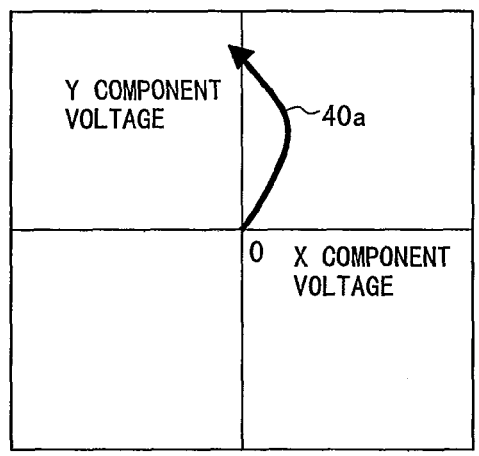
Figure 17C:
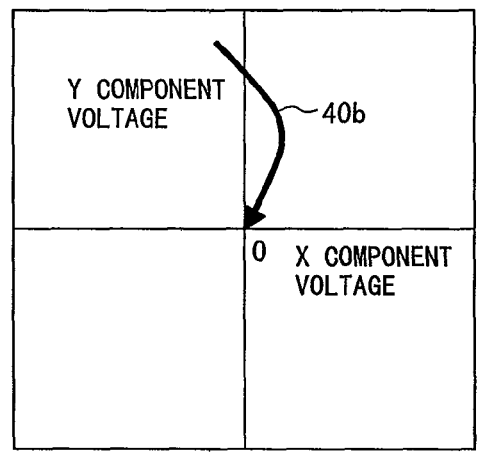

FIG. 16 is a block diagram showing the entire configuration of an eddy current testing device according to the present embodiment. In the FIG. 16, the same reference numerals as those in the first embodiment denote the same elements, and description thereof is omitted.

In FIG. 16, reference numeral 5A denotes an inspection controller according to the second embodiment. The inspection controller 5A has a difference processor 38. The difference processor 38 performs predetermined arithmetic processing on the following data (stored in the detection data storage section 19): detection data indicative of an X component voltage obtained from the first detection coil 9B; detection data indicative of a Y component voltage obtained from the first detection coil 9B; detection data indicative of an X component voltage obtained from the second detection coil 9C; and detection data indicative of a Y component voltage obtained from the second detection coil 9C. The difference processor 38 performs difference processing on a signal detected from a certain detection position (or at a certain time) and on a signal detected from a detection position close to the certain detection position (or at a time close to the certain time).

A signal detected by the eddy current probe 2 may have a lift-off signal and a flaw signal overlapped with the lift-off signal. As shown in a Lissajous diagram of FIG. 17A, the difference processor 38 differentiates between a signal Zn detected from a certain detection position and a signal Zn+1 detected from a detection position close to the certain detection position to remove an impact of a lift-off signal 39 and to thereby extract a flaw signal 40a. In this case, the positive indicator signal 40a and a negative indicator signal 40b are obtained as a flaw signal corresponding to a single crack (refer to FIGS. 17B and 17C). The detection data obtained from the first detection coil 9B is used as an example and is described below with reference to FIGS. 18A and 18B.

Figure 18A:
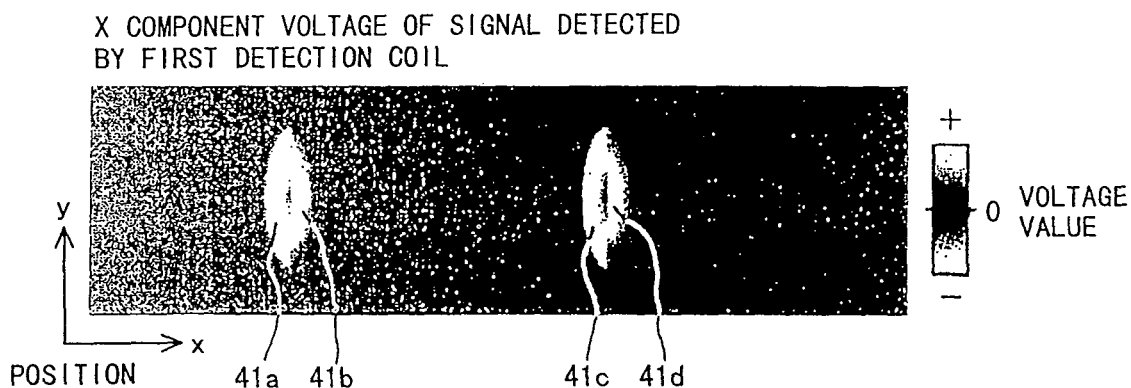
FIGS. 18A and 18B are diagrams showing an example of detection data subjected to difference processing by a difference processor provided in an inspection controller according to the second embodiment of the present invention.
Figure 18B:
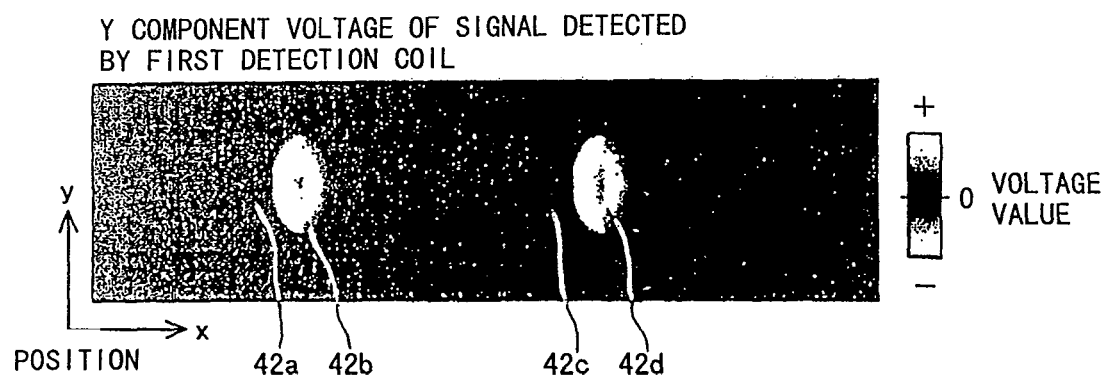

FIG. 18A shows the detection data indicative of the X component voltage, while FIG. 18B shows the detection data indicative of the Y component voltage. The detection data shown in FIGS. 18A and 18B is represented in two dimensional coordinates. In the two dimensional coordinates, the position of a portion of the target object (from which the signal is detected) in the lateral direction of the probe is plotted along an X axis, and the position of the portion of the target object (from which the signal is detected) in the longitudinal direction of the probe is plotted along a Y axis. In addition, the detection data shown in FIGS. 18A and 18B is represented as voltage image data. That is, voltage values of the detection data shown in FIGS. 18A and 18B are indicated by means of chromaticity (or brightness) of pixels. A positive voltage indicator signal 41a and a negative voltage indicator signal 41b appear in the detection data indicative of the X component voltage and correspond to the voltage indicator signal 24a shown in FIG. 4A. A positive voltage indicator signal 41c and a negative voltage indicator signal 41d appear in the detection data indicative of the X component voltage and correspond to the voltage indicator signal 24b shown in FIG. 4A. In addition, a positive voltage indicator signal 42a and a negative voltage indicator signal 42b appear in the detection data indicative of the Y component voltage and correspond to the voltage indicator signal 25a shown in FIG. 4B. A positive voltage indicator signal 42c and a negative voltage indicator signal 42d appear in the detection data indicative of the Y component voltage and correspond to the voltage indicator signal 25b shown in FIG. 4B.

The noise remover 20 removes a noise signal from the following detection data (subjected to the difference processing by the difference processor 38): the detection indicative of the X component voltage obtained from the first detection coil 9B; the detection data indicative of the Y component voltage obtained from the first detection coil 9B; the detection data indicative of the X component voltage obtained from the second detection coil 9C; and the detection data indicative of the Y component voltage obtained from the second detection coil 9C. After that, the phase angle calculator 21 calculates a phase angle of the signal detected by the first detection coil 9B and a phase angle of the signal detected by the second detection coil 9C for each detection position.

Figure 19A:
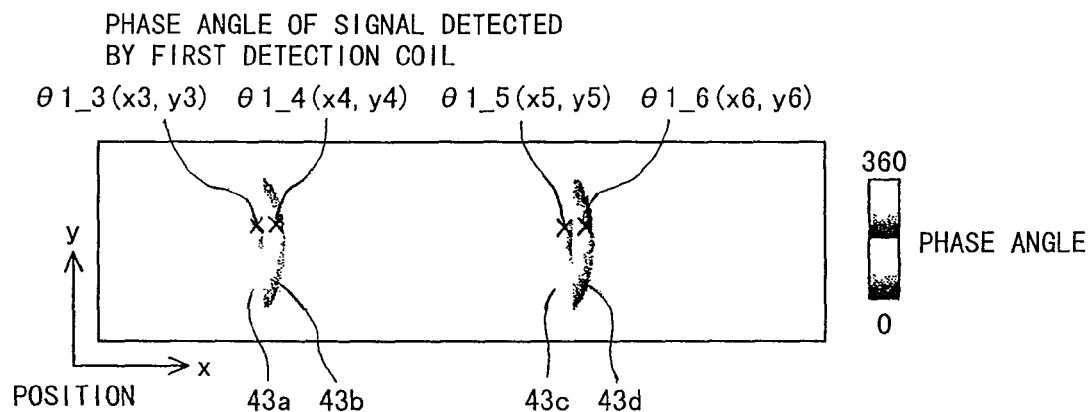
FIGS. 19A and 19B are diagrams showing an example of phase angle image data generated by the image data generator provided in the inspection controller according to the second embodiment of the present invention.
Figure 19B:
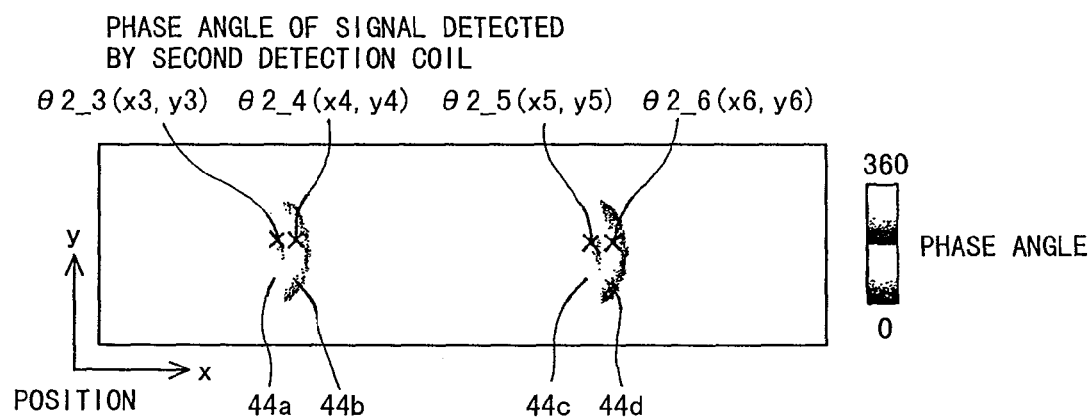

The image data generator 23 included in the inspection controller 5A has a first function (means for generating phase angle image data) for generating phase angle image data (refer to FIG. 19A). The phase angle image data indicates the phase angle of the signal detected by the first detection coil 9B by means of chromaticity (or brightness) of pixels in two dimensional coordinates. In the two dimensional coordinates, the position of a portion of the target object (from which the signal is detected) in the lateral direction of the probe is plotted along an X axis and the position of the portion of the target object (from which the signal is detected) in the longitudinal direction of the probe is plotted along a Y axis. Similarly, the image data generator 23 generates phase angle image data (refer to FIG. 19B) that indicates the phase angle of the signal detected by the second detection coil 9C. A phase angle indicator signal 43a, which is the result of a calculation based on the voltage indicator signals 41a and 42a, appears in the image data that indicates the phase angle of the signal detected by the first detection coil 9B. Also, a phase angle indicator signal 43b, which is the result of a calculation based on the voltage indicator signals 41b and 42b, appears in the image data that indicates the phase angle of the signal detected by the first detection coil 9B. In addition, a phase angle indicator signal 43c, which is the result of a calculation based on the voltage indicator signals 41c and 42c, appears in the image data that indicates the phase angle of the signal detected by the first detection coil 9B. Furthermore, a phase angle indicator signal 43d, which is the result of a calculation based on the voltage indicator signals 41d and 42d, appears in the image data that indicates the phase angle of the signal detected by the first detection coil 9B. Phase angle indicator signals 44a to 44d, which are respectively related to the detection positions from which the phase angle indicator signals 43a to 43d are obtained, appear in the image data that indicates the phase angle of the signal detected by the second detection coil 9C.

Figure 20:
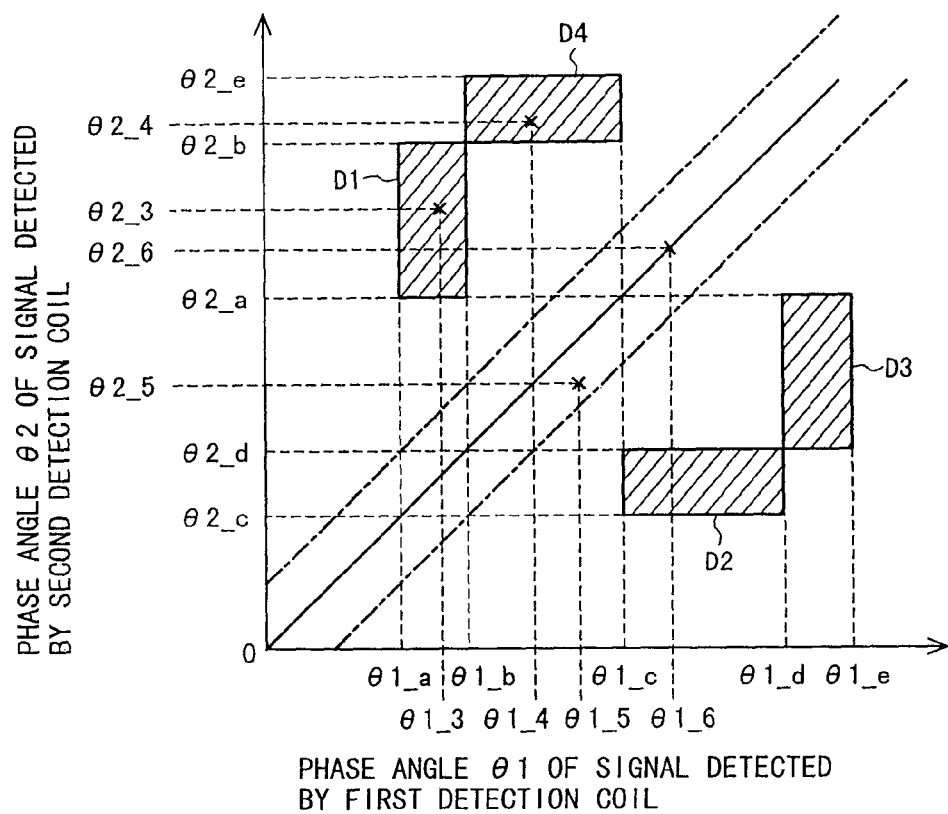
FIG. 20 is a diagram showing an example of an identification map stored in the identification map storage section provided in the inspection controller according to the second embodiment of the present invention.

The image data generator 23 included in the inspection controller 5A has a second function (means for determining a flaw signal) for performing predetermined arithmetic processing on the image data indicative of the phase angle of the signal detected by the first detection coil 9B and on the image data indicative of the phase angle of the signal detected by the second detection coil 9C to determine whether or not the detected signals (for example, the phase angle indicator signals 43a, 44a, the phase angle indicator signals 43b, 44b, the phase angle indicator signals 43c, 44c, and the phase angle indicator signals 43d, 44d) correspond to flaw signals. Specifically, the identification map storage section 22 has an identification map stored therein. The identification map includes predetermined standard areas D1, D2, D3 and D4 as shown in FIG. 20. The image data generator 23 reads the identification map from the identification map storage section 22. The image data generator 23 then determines whether or not the phase angle of the signal detected by the first detection coil 9B and the phase angle of the signal detected by the second detection coil 9C are included in the predetermined standard areas D1 to D4 for each detection position to determine whether or not the detected signals correspond to flaw signals. The details are described below.

For example, when a crack present on the target object extends in the longitudinal direction of the probe, the phase angle θ1 (of the signal detected by the first detection coil 9B) calculated based on the positive voltage indicator signals is 90 degrees, and the phase angle θ2 (of the signal detected by the second detection coil 9C) calculated based on the negative voltage indicator signals is 230 degrees. Therefore, a flaw signal corresponding to the crack extending in the longitudinal direction of the probe is included in an area defined by the expression of $\theta1\_a \leq \theta1 \leq \theta1\_b$ (for example, $80° \leq \theta1 \leq 100°$) and the expression of $\theta2\_a \leq \theta2 \leq \theta2\_b$ (for example, $180° \leq \theta2 \leq 260°$). That is, the flaw signal corresponding to the crack extending in the longitudinal direction of the probe is included in the predetermined standard area D1 on the identification map. In addition, the phase angle θ1 (of the signal detected by the first detection coil 9B) calculated based on the negative voltage indicator signals is 270 degrees (=360°−90°), and the phase angle θ2 (of the signal detected by the second detection coil 9C) calculated based on the positive voltage indicator signals is 130 degrees (=360°−230°). Therefore, a flaw signal corresponding to the crack extending in the longitudinal direction of the probe is included in an area defined by the expression of $\theta1\_d \leq \theta1 \leq \theta1\_e$ (for example, $260° \leq \theta1 \leq 280°$) and the expression of $\theta2\_d \leq \theta2 \leq \theta2\_a$ (for example, $100° \leq \theta2 \leq 180°$). That is, the flaw signal corresponding to the crack extending in the longitudinal direction of the probe is included in the predetermined standard area D3 on the identification map.

On the other hand, when a crack present on the target object extends in the lateral direction of the probe, the phase angle θ1 (of the signal detected by the first detection coil 9B) calculated based on the negative voltage indicator signals is 230 degrees, and the phase angle θ2 (of the signal detected by the second detection coil 9C) calculated based on the positive voltage indicator signals is 90 degrees. Therefore, a flaw signal corresponding to the crack extending in the lateral direction of the probe is included in an area defined by the expression of $\theta1\_c \leq \theta1 \leq \theta1\_d$ (for example, $180° \leq \theta1 \leq 260°$) and the expression of $\theta2\_c \leq \theta2 \leq \theta2\_d$ (for example, $80° \leq \theta2 \leq 100°$). That is, the flaw signal corresponding to the crack extending in the lateral direction of the probe is included in the predetermined standard area D2 on the identification map. In addition, the phase angle θ1 (of the signal detected by the first detection coil 9B) calculated based on the positive voltage indicator signals is 130 degrees (=360°−230°), and the phase angle θ2 (of the signal detected by the second detection coil 9C) calculated based on the negative voltage indicator signals is 270 degrees (=360°−90°). Therefore, a flaw signal corresponding to the crack extending in the lateral direction of the probe is included in an area defined by the expression of $\theta1\_b \leq \theta1 \leq \theta1\_c$ (for example, $100° \leq \theta1 \leq 180°$) and the expression of $\theta2\_b \leq \theta2 \leq \theta2\_e$ (for example, $260° \leq \theta2 \leq 280°$). That is, the flaw signal corresponding to the crack extending in the lateral direction of the probe is included in the predetermined standard area D4 on the identification map.

Since the image data generator 23 determines whether or not the phase angle of the signal detected by the first detection coil 9B and the phase angle of the signal detected by the second detection coil 9C are included in the standard areas D1 to D4, the flaw signal and other signals (lift-off signal and bending signal) can be distinguished. For example, a point obtained by combining a phase angle θ1_3 (x3, y3) (shown in FIG. 19A) of the signal detected by the first detection coil 9B at a detection position (x3, y3) with a phase angle θ2_3 (x3, y3) (shown in FIG. 19B) of the signal detected by the second detection coil 9C at the detection position (x3, y3) is included in the predetermined standard area D1 on the identification map. The image data generator 23 determines that the signal detected from the detection position (x3, y3) corresponds to a flaw signal. In addition, a point obtained by combining a phase angle θ1_4 (x4, y4) (shown in FIG. 19A) of the signal detected by the first detection coil 9B at a detection position (x4, y4) with a phase angle θ2_4 (x4, y4) (shown in FIG. 19B) of the signal detected by the second detection coil 9C at the detection position (x4, y4) is included in the predetermined standard area D2 on the identification map. The image data generator 23 determines that the signal detected from the detection position (x4, y4) corresponds to a flaw signal. A point obtained by combining a phase angle θ1_5 (x5, y5) (shown in FIG. 19A) of the signal detected by the first detection coil 9B at a detection position (x5, y5) with a phase angle θ2_5 (x5, y5) (shown in FIG. 19B) of the signal detected by the second detection coil 9C at the detection position (x5, y5) is not included in the predetermined standard areas D1 to D4 on the identification map. The image data generator 23 determines that the signal detected from the detection position (x5, y5) does not correspond to a flaw signal. A point obtained by combining a phase angle θ1_6 (x6, y6) (shown in FIG. 19A) of the signal detected by the first detection coil 9B at a detection position (x6, y6) with a phase angle θ2_6 (x6, y6) (shown in FIG. 19B) of the signal detected by the second detection coil 9C at the detection position (x6, y6) is not included in the predetermined standard areas D1 to D4 on the identification map. The image data generator 23 determines that the signal detected from the detection position (x6, y6) does not correspond to a flaw signal.

Figure 21:
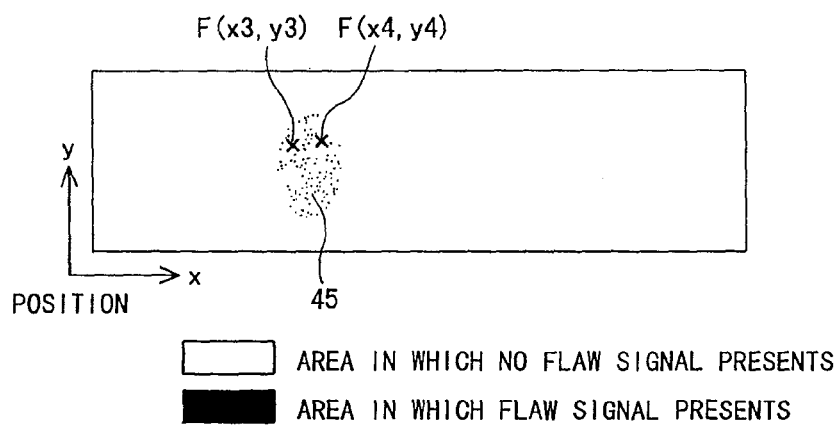
FIG. 21 is a diagram showing an example of flaw identification image data generated by the image data generator provided in the inspection controller according to the second embodiment of the present invention.

The image data generator 23 has a third function (means for generating flaw identification image data) for generating flaw identification image data (refer to FIG. 21). The flaw identification image data indicates an area 45 of the signal detected and determined to correspond to a flaw signal by the image data generator 23. The area 45 is represented in two dimensional coordinates in which the position of a portion of the target object (from which the signal is detected) in the lateral direction of the probe is plotted along as an X axis, and the position of the portion of the target object (from which the signal is detected) in the longitudinal direction of the probe is plotted along as a Y axis. The image data generator 23 outputs the flaw identification image data to the display unit 7. The display unit 7 then displays an image included in the flaw identification image data.

The thus configured eddy current testing device according to the present embodiment is capable of clearly displaying an area corresponding to a crack of a target object, easily confirming that the crack is detected, and specifying the position of a portion of the target object from which the crack is detected, like in the first embodiment.

The second embodiment describes the example in which the eddy current testing device has the difference processor 38 for performing the difference processing on detection data stored in the detection data storage section 19 as means for differentiating between a signal detected from a certain detection position (or at a certain time) and a signal detected from a detection position close to the certain detection position (or at a time close to the certain time). The second embodiment, however, is not limited to this. The eddy current probe may differentiate between the detected signals and output the differentiated detected signals. The same effect as the aforementioned effect can be obtained.

Each of the first and second embodiments describes the eddy current testing device that performs the predetermined arithmetic processing on the image data indicative of the phase angle of the signal detected by the first detection coil 9B and on the image data indicative of the phase angle of the signal detected by the second detection coil 9C; determines whether or not the detected signals correspond to flaw signals; generates flaw identification image data that indicates an area of the signal detected and determined to correspond to the flaw signal and is represented in the coordinates in which the position of the portion of the target object (from which the signal is detected) is plotted along the coordinate axis; outputs the flaw identification image data to the display unit 7; and causes the display unit 7 to display the flaw identification image data. The first and second embodiments, however, are not limited to this. The eddy current testing device according to each of the first and second embodiments may have a configuration in which the image data indicative of the signal detected by the first detection coil 9B and the image data indicative of the signal detected by the second detection coil 9C are output to the display unit 7 and displayed by the display unit 7. In this case, the inspector can refer to the identification map to determine whether or not the detected signals correspond to flaw signals.

According to each of the first and second embodiments, the multi-coil probe is used as the eddy current probe 2, and moved by the scanning mechanism 3 in a single direction. The eddy current probe, however, is not limited to this configuration. For example, the eddy current probe may have only one pair of the excitation coil and the detection coil and be moved by the scanning mechanism in multiple directions. In addition, the eddy current probe may be manually moved. In this case, the inspection controller generates image data indicative of coordinates representing the time when a signal is detected. In the above two cases, the aforementioned same effect can be obtained.

According to each of the first and second embodiments, the image data generator 23 provided in the inspection controller generates: image data that indicates the phase angle of the detected signal by means of chromaticity (or brightness) in the two dimensional coordinates (which are the X-Y coordinates in which the position of the portion of the target object (from which the signal is detected) is plotted along the coordinate axis); and flaw identification image data that indicates an area of the signal detected and determined to correspond to a flaw signal in the two dimensional coordinates (which are the X-Y coordinates in which the position of the portion of the target object (from which the signal is detected) is plotted along the coordinate axis). The first and second embodiments, however, are not limited to this. The image data generator 23 may generate image data represented in three dimensional coordinates in which the phase angle of each detected signal, and the area of the signal detected and determined to correspond to a flaw signal, may be plotted along a Z axis. In this case, the same effect as the aforementioned effect can be obtained.

According to each of the first and second embodiments, the noise remover 20 provided in the inspection controller uses the frequency filter to remove a noise signal. The first and second embodiments, however, is not limited to this. For example, when amplitude (or an X component voltage and a Y component voltage) of a noise signal is obtained in advance through testing, inspection or the like, a threshold value slightly larger than the amplitude (or the voltages) of the noise signal may be set previously, and the noise remover 20 may perform arithmetic processing to remove a signal having amplitude smaller than the set threshold value.

According to each of the first and second embodiments, the display unit 7 is used as means for outputting the image data generated by the image data generator 23 provided in the inspection controller. The first and second embodiments, however, are not limited to this. A printer may be used to print out the image data. In addition, the image data may be output to a storage medium, a communication section and the like, and then displayed by the display unit or printed out by the printer or the like via the storage medium, the communication section and the like. In this case, the aforementioned same effect can be obtained.

Each of the first and second embodiments describes the example in which a crack (a change in characteristics of a target object) is detected. The first and second embodiments, however, are not limited to this. For example, a change in a property of a material of the target object, or the like may be detected by the eddy current testing device according to the present invention.

What is claimed is:

1. An eddy current testing device comprising:
an eddy current probe for inspecting a change in characteristics of a target object;
phase angle calculation means for calculating a phase angle of a signal detected by said eddy current probe;
image data generator for generating image data which indicates the phase angle in coordinates in which at least one of the position of a portion from which the signal is detected, and a time when the signal is detected from the portion, is plotted along a coordinate axis, or generating image data which indicates information based on the phase angle in the coordinates; and
output means for outputting the image data generated by said image data generator, wherein
said eddy current probe has at least one excitation coil, a first detection coil and a second detection coil, the first detection coil being arranged adjacent to one side of the excitation coil and the second detection coil being arranged adjacent to another side of the excitation coil;
said phase angle calculation means calculates a first phase angle of a first signal detected by the first detection coil and a second phase angle of a second signal detected by the second detection coil;
said image data generator generates first image data and second image data, the first image data indicating the first phase angle in coordinates in which at least one of the position of a portion of the target object from which the first signal is detected, and a time when the first signal is detected from the portion, is plotted along a coordinate axis, the second image data indicating the second phase angle in coordinates in which at least one of the position of a portion of the target object from which the second signal is detected, and a time when the second signal is detected from the portion, is plotted along a coordinate axis; and
said output means outputs the first image data and the second image data, which are generated by said image data generator.

2. The eddy current testing device according to claim 1, further comprising noise removal means for removing a noise signal having a frequency within a preset predetermined frequency band or a noise signal having amplitude lower than preset predetermined amplitude from the first and second signals detected by said eddy current probe, wherein
said phase angle calculation means calculates the first and second phase angles of the first and second detected signals after the noise signal is removed from the first and second detected signals by the noise removal means.

3. The eddy current testing device according to claim 1, wherein
said image data generator generates image data which indicates the first and second phase angles of the first and second detected signals, which is calculated by said phase angle calculation means, by means of chromaticity or brightness of pixels.

4. The eddy current testing device according to claim 1, wherein
said eddy current probe has a flexible substrate mounting the excitation coil, the first detection coil and the second detection coil thereon.

5. An eddy current testing device comprising:
an eddy current probe for inspecting a change in characteristics of a target object;
phase angle calculation means for calculating a phase angle of a signal detected by said eddy current probe;
image data generator for generating image data which indicates the phase angle in coordinates in which at least one of the position of a portion from which the signal is detected, and a time when the signal is detected from the portion, is plotted along a coordinate axis, or generating image data which indicates information based on the phase angle in the coordinates; and
output means for outputting the image data generated by said image data generator, wherein
said eddy current probe has at least one excitation coil, a first detection coil and a second detection coil, the first detection coil being arranged adjacent to one side of the excitation coil and the second detection coil being arranged adjacent to another side of the excitation coil;
said phase angle calculation means calculates a first phase angle of a first signal detected by the first detection coil and a second phase angle of a second signal detected by the second detection coil;
said image data generator determines whether or not the first detected signal and the second detected signal correspond to a change in the characteristics of the target object, based on the relationship between the first phase angle and the second phase angle which are calculated by said phase angle calculation means, and generates image data which indicates an area of the detected signal determined to correspond to the change in the characteristics of the target object by the determination means in coordinates in which at least one of the position of a portion of the target object from which the signal is detected, and a time when the signal is detected from the portion, is plotted along a coordinate axis; and said output means outputs the image data generated by said image data generator.

6. The eddy current testing device according to claim 5, further comprising storage means for storing data which indicates a preset predetermined standard area in coordinates in which the first phase angle of the first signal detected by the first detection coil and the second phase angle of the second signal detected by the second detection coil are plotted along coordinate axes, wherein said image data generator determines whether or not the first and second detected signals correspond to the change in the characteristics of the target object by determining whether or not the first phase angle and the second phase angle, which are calculated by said phase angle calculation means, are included in the predetermined standard area stored by the storage means.

7. The eddy current testing device according to claim 5, wherein said eddy current probe has a flexible substrate mounting the excitation coil, the first detection coil and the second detection coil thereon.

8. An eddy current testing method for inspecting a change in characteristics of a target object by using an eddy current probe, the method comprises:

a first step of calculating a phase angle of a signal detected by the eddy current probe; and a second step of generating and outputting image data which indicates the phase angle of the detected signal in coordinates in which at least one of the position of a portion of the target object from which the signal is detected, and a time when the signal is detected from the portion, is plotted along a coordinate axis, or generating and outputting image data which indicates information based on the phase angle in the coordinates, wherein the eddy current probe has at least one excitation coil, a first detection coil and a second detection coil, the first detection coil being arranged adjacent to one side of the excitation coil and the second detection coil being arranged adjacent to another side of the excitation coil;

said first step is performed to calculate a first phase angle of a first signal detected by the first detection coil and a second phase angle of a second signal detected by the second detection coil; and said second step is performed to generate and output first image data which indicates the first phase angle of the first signal in coordinates in which at least one of the position of a portion of the target object from which the first signal is detected, and a time when the first signal is detected from the portion, is plotted along a coordinate axis, and generate and output second image data which indicates the second phase angle of the second signal in coordinates in which at least of the position of a portion of the target object from which the second signal is detected, and a time when the second signal is detected, is plotted along a coordinate axis.

9. An eddy current testing method for inspecting a change in characteristics of a target object by using an eddy current probe, the method comprises:

a first step of calculating a phase angle of a signal detected by the eddy current probe; and a second step of generating and outputting image data which indicates the phase angle of the detected signal in coordinates in which at least one of the position of a portion of the target object from which the signal is detected, and a time when the signal is detected from the portion, is plotted along a coordinate axis, or generating and outputting image data which indicates information based on the phase angle in the coordinates, wherein the eddy current probe has at least one excitation coil, a first detection coil and a second detection coil, the first detection coil being arranged adjacent to one side of the excitation coil and the second detection coil being arranged adjacent to another side of the excitation coil;

said first step is performed to calculate a first phase angle of a first signal detected by the first detection coil and a second phase angle of a second signal detected by the second detection coil; and said second step is performed to determine whether or not the first and second detected signals correspond to the change in the characteristics of the target object, based on the relationship between the first phase angle of the first detected signal and the second phase angle of the second detected signal, and generate and output image data which indicates an area of the signal detected and determined to correspond to the change in the characteristics of the target object in coordinates in which at least one of the position of a portion of the target object from which the signal is detected, and a time when the signal is detected from the portion, is plotted along a coordinate axis.

\* \* \* \* \*